(12) United States Patent
Chiu et al.

(10) Patent No.: US 10,794,925 B2
(45) Date of Patent: Oct. 6, 2020

(54) SYSTEMS, METHODS, AND DEVICES FOR SELF-DIGITIZATION OF SAMPLES

(71) Applicant: University of Washington, Seattle, WA (US)

(72) Inventors: Daniel T. Chiu, Seattle, WA (US); Bryant S. Fujimoto, Seattle, WA (US); Jason E. Kreutz, Seattle, WA (US)

(73) Assignee: University of Washington, Seattle, WA (US)

( * ) Notice: Subject to any disclaimer, the term of this patent is extended or adjusted under 35 U.S.C. 154(b) by 16 days.

(21) Appl. No.: 15/741,462

(22) PCT Filed: Jul. 7, 2016

(86) PCT No.: PCT/US2016/041369
§ 371 (c)(1),
(2) Date: Jan. 2, 2018

(87) PCT Pub. No.: WO2017/007954
PCT Pub. Date: Jan. 12, 2017

(65) Prior Publication Data
US 2018/0364270 A1  Dec. 20, 2018

Related U.S. Application Data

(60) Provisional application No. 62/189,663, filed on Jul. 7, 2015.

(51) Int. Cl.
*B01L 7/00* (2006.01)
*C12Q 1/686* (2018.01)
(Continued)

(52) U.S. Cl.
CPC ........ *G01N 35/1016* (2013.01); *B01L 3/5025* (2013.01); *B01L 3/502746* (2013.01);
(Continued)

(58) Field of Classification Search
None
See application file for complete search history.

(56) References Cited

U.S. PATENT DOCUMENTS 4,857,453 A   8/1989  Ullman et al.
5,061,381 A   10/1991 Burd
(Continued)

FOREIGN PATENT DOCUMENTS

CN       1427742 A    7/2003
CN     101384846 A    3/2009
(Continued)

OTHER PUBLICATIONS

Chinese office action dated Aug. 1, 2018 for Chinese application No. 201480042392.
(Continued)

*Primary Examiner* — Young J Kim
(74) *Attorney, Agent, or Firm* — Christensen O'Connor Johnson Kindness PLLC

(57) ABSTRACT

Systems, methods, and devices for discretizing and analyzing fluidic samples are provided. In one aspect, a microfluidic array for discretizing a fluidic sample comprises one or more flow channels and a plurality of fluidic compartments in fluidic communication with the one or more flow channels. In another aspect, a system for discretizing and analyzing fluidic samples comprises a rotor assembly shaped to receive a microfluidic device.

17 Claims, 16 Drawing Sheets

(51) Int. Cl.
| | |
|---|---|
| *G01N 35/10* | (2006.01) |
| *G01N 21/64* | (2006.01) |
| *G01N 35/00* | (2006.01) |
| *G01N 35/02* | (2006.01) |
| *G01N 35/04* | (2006.01) |
| *G01N 15/14* | (2006.01) |
| *B01L 3/00* | (2006.01) |
| *B01L 9/00* | (2006.01) |
| *G01N 15/10* | (2006.01) |

(52) U.S. Cl.
CPC ............... *B01L 7/52* (2013.01); *B01L 9/523* (2013.01); *C12Q 1/686* (2013.01); *G01N 15/1463* (2013.01); *G01N 21/6456* (2013.01); *G01N 35/00069* (2013.01); *G01N 35/025* (2013.01); *G01N 35/04* (2013.01); *B01L 2200/027* (2013.01); *B01L 2200/0673* (2013.01); *B01L 2300/0809* (2013.01); *B01L 2300/0816* (2013.01); *B01L 2300/0864* (2013.01); *B01L 2300/18* (2013.01); *B01L 2300/1894* (2013.01); *B01L 2400/0409* (2013.01); *G01N 2015/1006* (2013.01); *G01N 2035/00158* (2013.01); *G01N 2035/00356* (2013.01); *G01N 2035/00366* (2013.01); *G01N 2035/0449* (2013.01); *G01N 2035/1034* (2013.01)

(56) References Cited

U.S. PATENT DOCUMENTS

| | | |
|---|---|---|
| 6,124,138 A | 9/2000 | Woudenberg et al. |
| 6,499,499 B2 | 12/2002 | Dantsker et al. |
| 6,706,519 B1 | 3/2004 | Kellogg et al. |
| 7,338,760 B2 | 3/2008 | Gong et al. |
| 7,390,676 B2 | 6/2008 | Seul et al. |
| 8,062,903 B2 | 11/2011 | Chiu et al. |
| 8,277,759 B2 | 10/2012 | Sundberg et al. |
| 8,926,811 B2 | 1/2015 | Wu |
| 8,940,147 B1 | 1/2015 | Bartsch et al. |
| 9,180,453 B2 | 11/2015 | Chiu et al. |
| 2002/0187072 A1 | 12/2002 | Karp |
| 2003/0138941 A1 | 7/2003 | Gong et al. |
| 2003/0138973 A1 | 7/2003 | Wagner et al. |
| 2003/0152994 A1 | 8/2003 | Woudenberg et al. |
| 2004/0018116 A1 | 1/2004 | Desmond et al. |
| 2004/0163958 A1 | 8/2004 | Kao et al. |
| 2004/0219590 A1 | 11/2004 | Dickinson et al. |
| 2004/0241693 A1 | 12/2004 | Ricoul et al. |
| 2007/0003443 A1 | 1/2007 | Sandell et al. |
| 2007/0052781 A1 | 3/2007 | Fraden et al. |
| 2007/0092924 A1 | 4/2007 | Anderson |
| 2008/0014589 A1 | 1/2008 | Link et al. |
| 2009/0071833 A1 | 3/2009 | Gorfinkel et al. |
| 2009/0217742 A1 | 9/2009 | Chiu et al. |
| 2010/0015715 A1 | 1/2010 | Cho et al. |
| 2010/0041046 A1 | 2/2010 | Chiu et al. |
| 2011/0053151 A1 | 3/2011 | Hansen et al. |
| 2013/0065280 A1 | 3/2013 | Park et al. |
| 2013/0309780 A1 | 11/2013 | Meltzer et al. |
| 2014/0087386 A1 | 3/2014 | Chiu et al. |
| 2014/0138312 A1 | 5/2014 | Bunner et al. |
| 2014/0272981 A1 | 9/2014 | Yamana et al. |
| 2014/0360877 A1 | 12/2014 | Ramsey et al. |
| 2016/0096172 A1 | 4/2016 | Chiu et al. |
| 2016/0354777 A1 | 12/2016 | Chiu et al. |

FOREIGN PATENT DOCUMENTS

| | | |
|---|---|---|
| CN | 102187216 A | 9/2011 |
| JP | 2014-153065 A | 8/2014 |
| JP | 2015-516085 A | 6/2015 |
| KR | 20020096070 A | 12/2002 |
| WO | WO-2007013562 A1 | 2/2007 |
| WO | WO-2007116909 A1 | 10/2007 |
| WO | WO-2008083526 A1 | 7/2008 |
| WO | WO-2010019388 A2 | 2/2010 |
| WO | WO-2010019388 A3 | 5/2010 |
| WO | WO-2012033765 A1 | 3/2012 |
| WO | 2012/170756 A1 | 12/2012 |
| WO | 2013/119765 A1 | 8/2013 |
| WO | WO-2014210207 A1 * | 12/2014 |
| WO | WO-2017007954 | 1/2017 |

OTHER PUBLICATIONS

European search report with written opinion dated Feb. 5, 2019 for EP Application No. 16821991.
Notice of allowance dated Jan. 2, 2019 for U.S. Appl. No. 14/869,871.
Office action dated Jul. 24, 2018 for U.S. Appl. No. 14/869,871.
Office action dated Nov. 2, 2018 for U.S. Appl. No. 14/900,926.
Hatch et al. 1-Million droplet array with wide-field fluorescence imaging for digital PCR, Lab on a Chip, 11(22):3838-3845 (2011).
"JP 2016-521913 Office Action dated May 1, 2018 (w/ English translation)".
Shen et al. Digital PCR on a SlipChip. Lab Chip 10:2666-2672 (2010).
Song et al. A nanoliter self-priming compartmentalization chip for point-of-care digital PCR analysis, Biomedical Microdevices, 17:64, 8 pages (2015.
Tanaka et al. Hands-Off Prepration of Monodisperse Emulsion Droplets Using a Poly(dimethlsiloxane) Microfluidic Chip for Droplet Digital PCR, Anal. Chem. 87(8):4134-4143 (2015).
Adamo, et al. Microfluidic based single cell microinjection. Lab Chip, Jul. 1, 2008, 8:1258-1261.
Biebuyck, et al. Self-Organization of Organic Liquids on Patterned Self-Assembled Monolayers of Alkanethiolates on Gold. Langmuir, 1994, 10: 2790-2793.
European search report and opinion dated Mar. 13, 2014 for EP Application No. 09807058.4.
Extended European search report and opinion dated Jan. 2, 2017 for EP Application No. 14817344.
International search report and written opinion dated Mar. 11, 2010 for PCT/US2009/052299.
International search report and written opinion dated Sep. 23, 2016 for PCT Application No. US-2016041369.
International search report and written opinion dated Oct. 20, 2014 for PCT/US2014/044167.
Jackman, et al. Fabricating Large Arrays of Microwells with Arbitrary Dimensions and Filling Them Using Discontinuous Dewetting. Anal. Chem., 1998, 70(11): 2280-2287.
Lorenz et al. Microfluidic and Optical Systems for the On-Demand Generation and Manipulation of Single Femtoliter-Volume Aqueous Droplets, Anal. Chern. 2006, vol. 78, No. 18, pp. 6433-9.
Morrison et al. Nanoliter high through quantitative PCR. Nucleic Acids Res 34(18):e123 (2006).
U.S. Appl. No. 14/900,926, Office Action dated Jan. 9, 2018.
U.S. Appl. No. 14/869,871, Office Action dated Aug. 21, 2017.
U.S. Appl. No. 14/900,926, Office Action dated Sep. 14, 2017.
CN 201480042392.6 Office Action dated Nov. 6, 2017. (w/ English translation).
U.S. Appl. No. 14/869,871, Office Action dated Jan. 20, 2017.
Ottesen et al. Microfluidic digital PCR enables multigene analysis of individual environmental bacteria. Science 314(5804):1464-1467 (2006).
Pollack, et al. Electrowetting-based actuation of liquid droplets for microfluidic applications. Appl. Phys. Lett., 2000, 77:1725.
Rossi, et al., Tapered Microfluidic Chip for the Study of Biochemical and Mechanical Response At Subcellular Level of Endothelial Cells to Shear Flow, Lab on a Chip, 2009, 9(10):1403-11.
Sgro et al. Thermoelectric Manipulation of Aqueous Droplets in Microfluidic Devices, Anal. Chern. 2007, vol. 79, No. 13, pp. 4848-4851.
Shi et al Droplet-based microfluidic system for individual Caenorhabditis elegans assay Lab Chip, 2008, 8: 1432-1435.

(56) References Cited

OTHER PUBLICATIONS

Unger, et al. Monolithic microfabricated valves and pumps by multilayer soft lithography. Science. 2000; 288:113-116.
U.S. Appl. No. 14/869,871, Office Action dated Jan. 26, 2018.
Wu, et al., Fabrication of microchannels using polynorbornene photosensitive sacrificial materials, J. of the electrochemical society, 2003,150(9):H205-H213.
Office Action dated Jul. 3, 2020, for Chinese Patent Application No. 201680051564.5. (with English translation, 23 pages).
Office Action dated Jun. 19, 2020, for Japanese Patent Application No. 2018-500411. (with English translation, 21 pages).

* cited by examiner

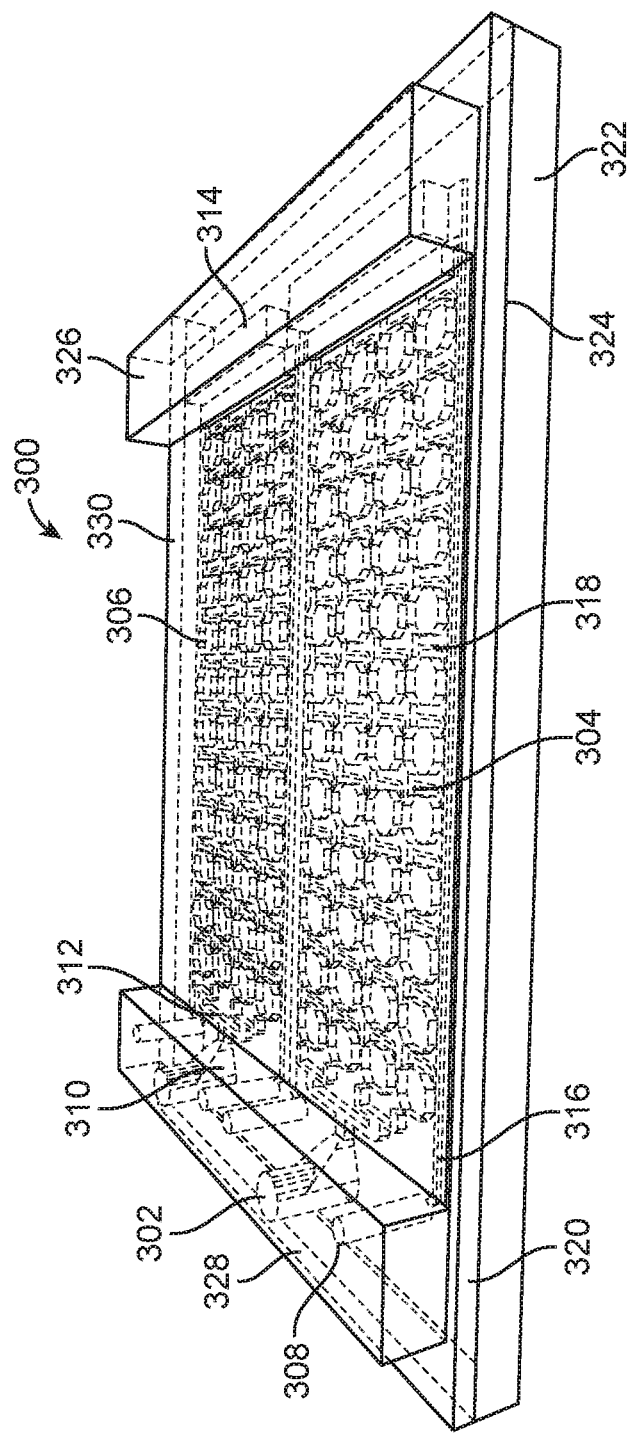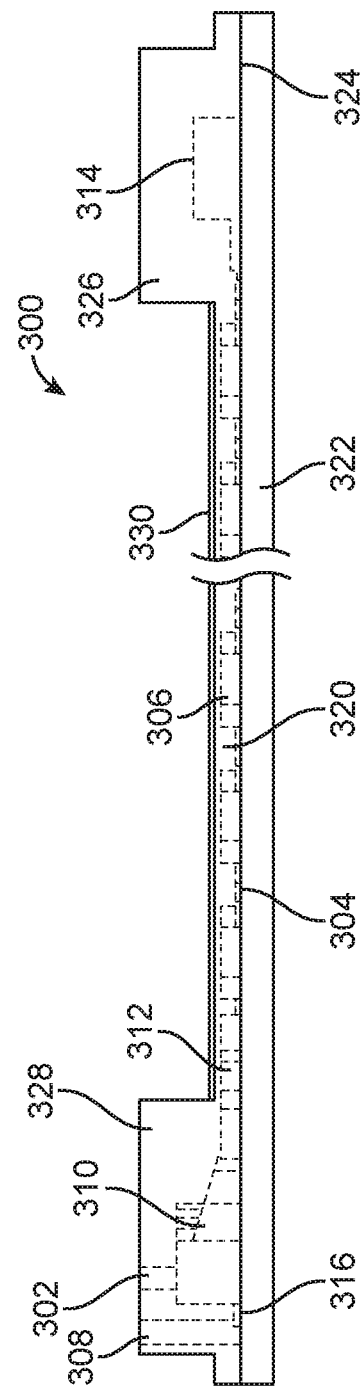

SYSTEMS, METHODS, AND DEVICES FOR SELF-DIGITIZATION OF SAMPLES

CROSS-REFERENCE TO RELATED APPLICATIONS

This application is a U.S. National Phase Application under 35 U.S.C. § 371 of International Application No. PCT/US2016/041369, filed Jul. 7, 2016, which claims the benefit of U.S. Provisional Application No. 62/189,663, filed Jul. 7, 2015, the disclosures of which are herein incorporated by reference in their entireties.

STATEMENT AS TO FEDERALLY SPONSORED RESEARCH

This invention was made with U.S. Government support under R21 GM103459, awarded by the National Institutes of Health. The U.S. Government has certain rights in the invention.

BACKGROUND

Discretization of samples into small fluidic compartment-defined volumes, also referred to herein as "self-digitization," is valuable in many chemical and biological applications. Prior mechanisms for self-digitization of samples, however, can be less than ideal in at least some instances. For instance, nebulizers and agitation-based emulsion generators may not provide sufficient control for some applications. Methods based on microfluidic technologies may be less than optimal with respect to complexity and cost. In some instances, prior approaches may not be adapted for high-throughput processing and analysis of large numbers of fluidic samples in parallel.

Thus, there is a need for improved systems, methods, and devices for self-digitization and manipulation of samples. The present disclosure addresses this need and more.

SUMMARY

The present disclosure provides systems, methods, and devices for discretizing and analyzing fluidic samples.

In various aspects, the present disclosure provides a microfluidic array for discretizing a fluidic sample, the array comprising: a proximal array portion comprising a fluid inlet port and a fluid outlet port; a distal array portion away from the proximal portion, one or more flow channels each comprising a length extending from the proximal array portion to the distal array portion; a proximal end in fluidic communication with the fluid inlet port, and a distal end in fluidic communication with the fluid outlet port, wherein at least one flow channel comprises a decreasing cross-sectional dimension along the length from the proximal array portion to the distal array portion; and a plurality of fluidic compartments in fluidic communication with the one or more flow channels.

In various aspects, the present disclosure provides a microfluidic array for discretizing a fluidic sample, the array comprising: a proximal array portion comprising a fluid inlet port and a fluid outlet port; a distal array portion away from the proximal portion, one or more flow channels each comprising a length extending from the proximal array portion to the distal array portion; a proximal end in fluidic communication with the fluid inlet port, and a distal end in fluidic communication with the fluid outlet port, wherein at least one flow channel comprises an increasing or substantially constant cross-sectional dimension along the length from the proximal array portion to the distal array portion; and a plurality of fluidic compartments in fluidic communication with the one or more flow channels.

In various aspects, the present disclosure provides a microfluidic device for discretizing a fluidic sample, the device comprising: a body comprising a proximal body portion and a distal body portion; and a plurality of microfluidic arrays as in any of the embodiments herein formed in the body such that the one or more flow channels of the plurality of microfluidic arrays extend substantially parallel to each other from the proximal body portion to the distal body portion.

In various aspects, the present disclosure provides a system for discretizing and analyzing fluidic samples, the system comprising: a rotor assembly comprising a central axis and a plurality of receptacles arranged radially around the central axis, each receptacle being shaped to receive a microfluidic device as in any of the embodiments herein such that the proximal body portion of the microfluidic device is positioned near the central axis and the distal body portion of the microfluidic device is positioned away from the central axis; a rotary actuator coupled to the rotor assembly; and one or more processors configured with instructions to cause the system to rotate the rotor assembly around the central axis using the rotary actuator.

In various aspects, the present disclosure provides a method for discretizing a fluidic sample, the method comprising providing a device as in any of the embodiments herein.

In various aspects, the present disclosure provides a method for discretizing a fluidic sample, the method comprising providing a system as in any of the embodiments herein.

In various aspects, the present disclosure provides a method for discretizing and analyzing a fluidic sample, the method comprising: providing a microfluidic device as in any of the embodiments herein; applying a fluidic sample to the fluid inlet ports of the microfluidic device, the fluidic sample comprising a plurality of discrete analytes; and rotating the microfluidic device such that the plurality of discrete analytes are driven into a subset of the plurality of fluidic compartments of the microfluidic device.

This summary is provided to introduce a selection of concepts in simplified form that are further described below in the Detailed Description. This summary is not intended to identify key features of the claimed subject matter, nor is it intended to be used as an aid in determining the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A illustrates a perspective view of a microfluidic device for self-digitization of fluidic samples.

FIG. 3B illustrates a side view of the device of FIG. 3A.

DETAILED DESCRIPTION

Figure 1:
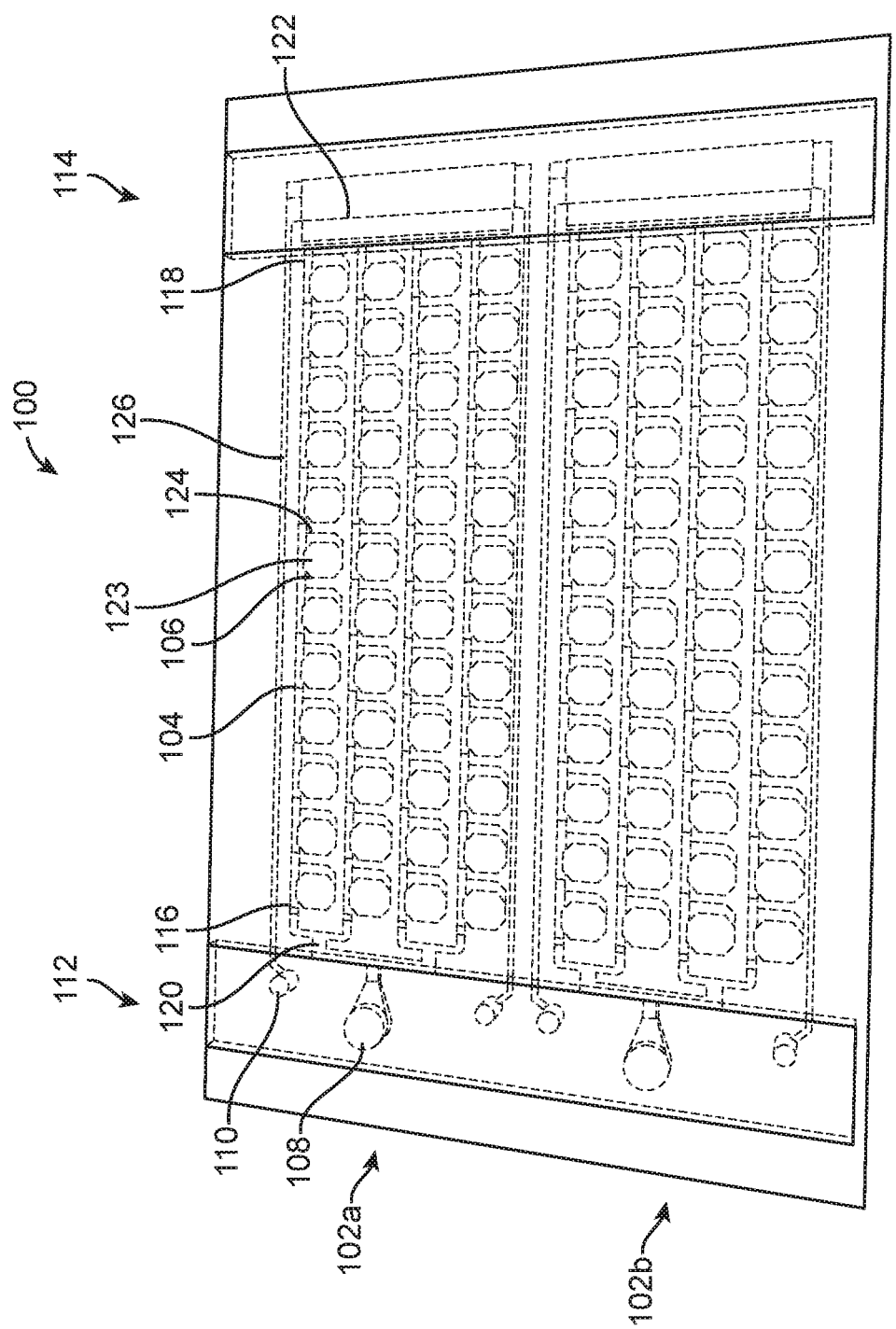
FIG. 1 illustrates a microfluidic device for self-digitization of a fluidic sample.

The present disclosure relates generally to systems, methods, and devices for self-digitization (also referred to herein as "digitization" or "discretization") of fluidic samples into small sample volumes. In some embodiments, a microfluidic device for discretizing a fluidic sample includes a plurality of fluidic compartments, and the fluidic sample is discretized into a plurality of discrete sample volumes defined by the fluidic compartments. In certain embodiments, the microfluidic device is configured for centrifugal sample loading, thus improving ease and flexibility of sample processing. For instance, in certain embodiments, the fluidic compartments are in fluidic communication with a tapering flow channel shaped to facilitate substantially uniform fluid flow, which provides improved reliability and control of the self-digitization procedure. Additionally, some embodiments of the present disclosure enable sample discretization, processing, and analysis to be performed using a single rotor-based device. The approaches presented herein provide high-throughput and low cost processing of fluidic samples compatible with a wide variety of analytical techniques.

Some embodiments of the present disclosure include systems, methods, and devices for the analysis of species that include, but are not limited to, chemicals, biochemicals, genetic materials, or biological cells. Potential applications for embodiments of the present disclosure include but are not limited to: polymerase chain reaction (PCR), digital polymerase chain reaction (dPCR), nucleic acid sequence-based amplification including isothermal amplification (e.g., loop mediated isothermal amplification (LAMP) and nucleic acid sequence-based amplification (NASBA)), crystallization of proteins and small molecules, and the analysis of cells (e.g., rare cells or single cells) or biological particles (e.g., isolated mitochondria) present in biological fluids. In some embodiments, the systems, methods, and devices of the present disclosure can be used for polymerase chain reaction (PCR), reverse transcriptase PCR (RT-PCR), ligase chain reaction (LCR), loop mediated amplification (LAMP) (RT-LAMP), helicase dependent amplification (HDA) (RT-HDA), recombinase polymerase amplification (RPA) (RT-RPA), and/or strand displacement amplification (SDA) (RT-SDA). In certain embodiments, the systems, methods, and devices of the present disclosure can be used for nucleic acid sequence based amplification (NASBA), transcription mediated amplification (TMA), self-sustained sequence replication (3SR), and single primer isothermal amplification (SPIA). Other techniques that can be used include, e.g., signal mediated amplification of RNA technology (SMART), rolling circle amplification (RCA), hyper branched rolling circle amplification (HRCA), exponential amplification reaction (EXPAR), smart amplification (SmartAmp), isothermal and chimeric primer-initiated amplification of nucleic acids (ICANS), and multiple displacement amplification (MDA).

Microfluidic Arrays for Self-Digitization of Fluidic Samples

In some embodiments of the present disclosure, a microfluidic device for self-digitization of a fluidic sample includes a plurality of fluidic components (e.g., compartments, reservoirs, channels, inlets, outlets, etc.), at least some of which are in fluidic communication with each other. As used herein, the terms "in fluidic communication with" and "fluidly coupled to" (and variations thereof) refers to the existence of a fluid path between components, and neither implies nor excludes the existence of any intermediate structures or components, nor implies that a path is always open or available for fluid flow.

FIG. 1 illustrates a microfluidic device 100 for self-digitization of a fluidic sample, in accordance with embodiments. The device 100 includes one or more microfluidic arrays, e.g., a first microfluidic array 102a and a second microfluidic array 102b. In certain embodiments, different microfluidic arrays are used to discretize different samples and thus are not in fluidic communication with each other. In some embodiments, the microfluidic array (e.g., microfluidic array 102a) includes one or more flow channels 104, a plurality of fluidic compartments 106, one or more fluid inlet ports 108, and one or more fluid outlet ports 110. In some embodiments, the one or more flow channels 104 each have a length extending from a proximal portion 112 of the array to a distal portion 114 of the array. In some embodiments, the arrays of the microfluidic device 100 are filled by centrifugal loading, as discussed further herein, and the orientation of the array is defined relative to the axis of rotation such that "proximal" refers to the direction towards the axis of rotation and "distal" refers to the direction away from the axis of rotation. In such embodiments, centrifugation is used to drive fluid from the proximal portion 112 of the array to the distal portion 114 of the array.

In some embodiments, each flow channel 104 includes a proximal end 116 in fluidic communication with the one or more fluid inlet ports 108 and a distal end 118 in fluidic communication with the one or more fluid outlet ports 110. Optionally, in embodiments where a plurality of flow channels 104 are used, one or more branching channels 120 are used to couple the inlet port(s) 108 to the proximal end 116 of each flow channel 104. In some embodiments, the distal ends 118 of the flow channels 104 are each coupled to the outlet port(s) 110 via an outlet reservoir 122 configured to contain a relatively large volume of fluid (e.g., compared to the sample volumes of the fluidic compartments 106). In certain embodiments, the reservoir 122 is used to contain excess fluid during the filling procedure, as discussed further herein. Similarly, in some embodiments, an inlet reservoir is provided between the inlet port(s) 108 and the proximal ends 116 of the flow channels 104.

The fluidic compartments 106 are each coupled to the one or more flow channels 104 via a respective opening conduit 123. In some embodiments, the fluidic compartments are positioned along the length of a corresponding flow channel 104 between the proximal ends 116 and distal ends 118. Accordingly, a fluid sample loaded into the array via the outlet port(s) 110 is distributed into the fluidic compartments 106 via the flow channels 104 and is thereby discretized into individual sample volumes. In some embodiments, centrifugation is used to drive fluid into the fluidic compartments 106, as discussed further herein. Optionally, each fluidic compartment 106 also includes at least one drainage channel 124 coupling the compartment 106 to the flow channel 104. In some embodiments, drainage channels are used to control the filling rate of the fluidic compartments 106 and/or the completeness of filling.

In some embodiments, the inlet port(s) 108 and outlet port(s) 110 are both situated at or near the proximal array portion 112, with the reservoir 122 situated at the distal array portion 114. In such embodiments, one or more outlet return channels 126 extending from the distal portion 114 to the proximal portion 112 are used to fluidly couple the reservoir 122 to the outlet port(s) 108. In alternative embodiments, the inlet port(s) 108 are situated at the proximal portion 112 and the distal port(s) 110 are situated at the distal portion 114, or vice-versa. The arrangement in which both the inlet port(s) 108 and outlet port(s) 110 are at the proximal portion 112 provides certain advantages for centrifugal loading. For instance, in some embodiments, having the outlet port(s) 110 at the proximal portion 112 near the axis of rotation causes flow rates to slow as the reservoir 122 fills up, as the fluid is unable to escape through the outlet(s) 110. This design feature provides a self-metering mechanism in which a set volume of fluid will pass through the fluidic compartment region before flow is automatically stopped. In various embodiments, this approach also reduces the likelihood of inadvertent leakage of the sample from the outlet port(s) 110 during centrifugation.

The design of the microfluidic arrays described herein can be varied as desired. For instance, in some embodiments, a microfluidic array includes at least 100, at least 500, at least 1000, at least 5000, at least 10,000, at least 50,000, at least 100,000, at least 500,000 or at least 1 million fluidic compartments. In certain embodiments, each fluidic compartment has a volume of approximately 5 pL, 10 pL, 50 pL, 100 pL, 500 pL, 1 nL, 5 nL, 10 nL, 50 nL, 100 nL, or 500 nL, or within a range from about 5 pL to about 500 nL. Various types of fluidic compartments are suitable for use within the embodiments herein. Fluidic compartments can take on various geometries, including but not limited to shapes where the cross section is circular, oval, square, rectangular, triangular, or some other polygonal shape, or combinations thereof. In certain embodiments, a fluidic compartment has rounded or beveled corners. Some fluidic compartments have symmetrical geometries, while others are asymmetrical in shape.

The fluidic compartments of a microfluidic device can be positioned in many different orientations, e.g., relative to the flow channel. In certain embodiments, the fluidic compartments are connected to the top or bottom of the flow channel ("top-harbor" or "bottom-harbor" design). In other embodiments, the fluidic compartments are connected to one or more sides of the flow channel ("side-harbor" design). In certain embodiments, the "long" axis of the fluidic compartment (the direction of the longest dimension of the fluidic compartment) still runs parallel to the main axis, but the compartment is offset from the channel. In other embodiments, the long axis of the compartment is perpendicular to the flow channel. In other embodiments, the "long" axis is positioned at some other angle relative to the flow axis. A fluidic compartment can be said to be offset from an axis of flow through the flow channel if a line drawn between the center of compartment and the centerline of the flow channel is longer than the shortest distance between a channel wall and its centerline.

In certain embodiments with fluidic compartments on the top/bottom of the flow channels, the vertical dimension (e.g., height) is increased. For instance, in some embodiments with fluidic compartments on the sides of the flow channel, both the vertical and a lateral dimension (e.g., length or width) are increased. In certain embodiments, the fluidic compartments are located on just one side of the flow channel. In other embodiments, the fluidic compartments are located on two sides of the flow channel. Having fluidic compartments on two sides of the flow channel can apply to both side- and bottom-harbor designs, and in certain embodiments fluidic compartments are positioned on three or four sides.

In some embodiments of the present disclosure, the fluidic compartments of a microfluidic array function to discretize samples via geometric differences between the fluidic compartments and the flow channels and/or because of positional differences between the fluidic compartments and the channels (e.g., the fluidic compartments are offset from the channels). In certain embodiments, one or more of the fluidic compartment dimensions (e.g., length, width, height, cross-sectional area) is greater than a corresponding dimension in the flow channel. In such embodiments, the differences between the fluidic compartment dimensions and the corresponding dimensions of the flow channel facilitate the expansion of an fluidic sample loaded on the device into the larger volume of the fluidic compartment. Without being bound by theory, it is believed that this expansion occurs spontaneously because the larger dimensions in the fluidic compartment lowers the interfacial energy between the two fluids relative to what they are in the flow channel.

In certain embodiments comprising fluidic compartments above or below the flow channels, the vertical dimension of the fluidic compartments, or height, is larger than the height of the channel. For instance, in some embodiments with fluidic compartments on the sides of the flow channel, both the vertical and a lateral dimension of the fluidic compartment are larger than the same flow channel dimensions.

In certain embodiments, the space between the downstream end of one of the fluidic compartments and the upstream end of a downstream fluidic compartment is between 0.1 and 3.0 times the length of the fluidic compartments. In certain embodiments, the space between the downstream end of one of the fluidic compartments and the upstream end of a downstream fluidic compartment is between 0.1 and 1 times the length of the fluidic compartments.

In certain embodiments, the width of the flow channel is greater than the width of the fluidic compartments. In certain embodiments, the difference between the width of the flow channel and the width of the fluidic compartments is between 0.001 and 3 times the width of the fluidic compartments. In certain embodiments, the difference between the width of the flow channel and the width of the fluidic compartments is between 0.01 and 1.5 times the width of the fluidic compartments.

In certain embodiments, additional constrictive or expansive features in the flow channel are used to facilitate transport of sample to fluidic compartments and to discretize samples within the compartments. For example, the fluidic compartments and/or the flow channels can be designed to have various dimensions according to a desired application. In certain embodiments, the fluidic compartment overlap with the channel, while in other embodiments, the fluidic compartment are flush with the channel wall, and in yet other embodiments, the fluidic compartment are connected to the channel by a protrusion. Alternatively, or in addition to these connections, indents in the channel can in effect recreate overlap with the channel or the use of a protrusion or a flush meeting of the channel and fluidic compartment, without adjusting the position of the fluidic compartment relative to the flow axis of the channel. In certain embodiments, these additional channel features (e.g., indents or protrusions) in the channel are used to redirect flow and/or to help isolate fluidic compartments. The indents and protrusions can have various shapes and sizes to suit particular performance requirements. In certain embodiments, such as side-harbor designs, the features are on the same side of the channel as the connection with the fluidic compartment. In some embodiments, constrictive or expansive features are located on the opposite side of the channel. In other embodiments, there are features on other channel sides as well. In certain embodiments, such as in bottom-harbor designs, the constrictive or expansive features are adjacent to the bottom compartments but in the plane of the channel.

The designs of the flow channels of the microfluidic arrays described herein can be varied as desired. In some embodiments, a microfluidic array includes at least 1, at least 2, at least 3, at least 4, at least 5, at least 6, at least 7, at least 8, at least 9, at least 10, at least 16, at least 32, at least 64, at least 128, at least 256, at least 512, at least 1024, at least 2048, at least 4096, or at least 8192 flow channels. In some embodiments, the flow channels are arranged to extend parallel or substantially parallel to each other. In alternative embodiments, some or all of the flow channels do not extend parallel to each other. A flow channel can be linear, curved, or curvilinear, as desired. In some embodiments, a microfluidic array includes only parallel linear flow channels, and such arrays are referred to herein as "linear microfluidic arrays." A flow channel can have a wide variety of cross-sectional shapes, such as a rectangular, trapezoidal, circular, semi-circular, oval, semi-oval, square, or triangular cross-sectional shape. In some embodiments, a flow channel has a single uniform cross-sectional shape throughout the length of the channel, while in other embodiments, the cross-sectional shape is variable along the length of the channel.

Tapering Flow Channels

In some embodiments, at least one flow channel of a microfluidic array has at least one decreasing cross-sectional dimension (e.g., width, length, height, area) along the length of the channel, e.g., from the proximal to the distal end of the channel and/or from the proximal to the distal portion of the array. In certain embodiments, "along the length of the channel" refers to along the portion of the channel that spans the entirety of the fluidic compartments coupled to the channel. Channels exhibiting a decreasing cross-sectional dimension along the length of the channel are also referred to herein as "tapering flow channels." In some embodiments, only a subset of the flow channels of a microfluidic array are tapering flow channels, such that at least some of the flow channels of the systems and devices herein do not exhibit tapering. In alternative embodiments, all of the flow channels of a microfluidic array are tapering flow channels, such that each of the flow channels exhibits tapering. The proportion of tapering and non-tapering channels in a microfluidic array can be varied as desired, e.g., such that approximately 0%, approximately 10%, approximately 20%, approximately 30%, approximately 40%, approximately 50%, approximately 60%, approximately 70%, approximately 80%, approximately 90%, or approximately 100% of the channels of the array exhibit tapering. In some embodiments, the cross-sectional dimension of at least one flow channel decreases according to a tapering profile configured to produce substantially uniform fluid flow rates and/or increasing flow resistance along the length of the flow channel. In some embodiments, the use of flow channels configured to produce substantially uniform fluid flow and/or increasing flow resistance improves control and consistency of compartment filling.

In some embodiments, the tapering profile of the cross-sectional dimension is determined based on the following relation for centrifugal microfluidic systems:

$$U=(D_h^2 \rho \omega^2 \bar{r} \Delta r)/(32 \mu L)$$

where U is the flow velocity, $D_h$ is the hydraulic diameter of the channel ($D_h^2=4AP$ where A is the cross-sectional area of the channel and P is the perimeter of the channel), $\rho$ is the density of the fluid, $\omega$ is the angular velocity of the fluid, $\bar{r}$ is the average distance of the fluid in the channel to the axis of rotation, $\Delta r$ is the radial extent of the fluid, $\mu$ is the viscosity of the fluid, and L is the length of the fluid in the channel. The volumetric flow rate Q is related to the flow velocity U and cross-sectional area A by the relation Q=UA.

In some embodiments, the tapering profile of the cross-sectional dimension is a continuous tapering profile without discontinuities (e.g., breaks, steps, etc.). For instance, a continuous tapering profile can be a linear tapering profile that decreases linearly, an exponential tapering profile that decreases exponentially, a polynomial tapering profile that decreases according to a polynomial function, or combinations thereof (e.g., some portions taper linearly while other portions taper exponentially, etc.). In other embodiments, the tapering profile of the cross-sectional dimension is a discontinuous tapering profile, e.g., a stepped tapering profile that decreases according to a step function. Optionally, in certain embodiments, the tapering profile includes a combination of one or more portions with continuous tapering and one or more portions with discontinuous tapering.

As an example, in some embodiments, some or all of the flow channels presented herein have a decreasing cross-sectional width along the length of the channel. In certain embodiments (e.g., when the cross-sectional width varies along the height of the channel), a decrease in cross-sectional width is determined with respect to an average cross-sectional width, a maximum cross-sectional width, and/or a minimum cross-sectional width of the flow channel.

Figure 2:
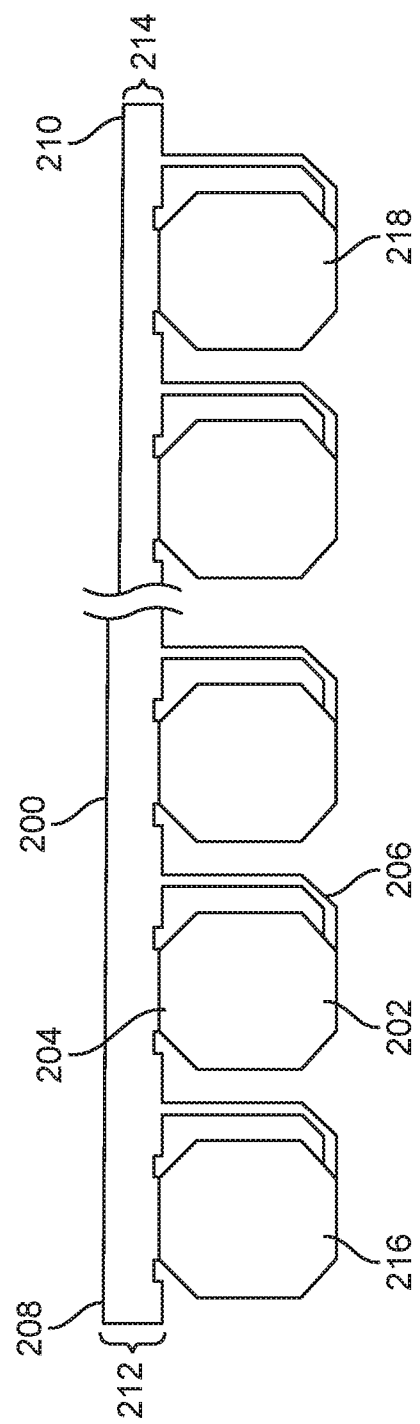
FIG. 2 schematically illustrates a flow channel with a decreasing cross-sectional width.

FIG. 2 schematically illustrates a flow channel 200 of a microfluidic array with a decreasing cross-sectional width, in accordance with embodiments. The flow channel 200 is suitable for use with any embodiment of the systems, methods, and devices presented herein. The flow channel 200 is coupled to each of a plurality of fluidic compartments 202 via a respective opening conduit 204 and drainage channel 206. The fluidic compartments 202 are distributed along the length of the flow channel 200 between the proximal end 208 and distal end 210 of the flow channel 200. As discussed above and herein, in embodiments where centrifugal filling is used, the proximal end 208 of the flow channel 200 is oriented towards the axis of rotation and the distal end 210 is located away from the center of location, such that fluid is driven along the length of the flow channel 200 and into the fluidic compartments 202 along a proximal-distal direction. In some embodiments, the flow channel 200 comprises a cross-sectional width 212 at or near the proximal end 208 greater than a cross-sectional width at or near the distal end 214. As used herein, "at or near the proximal end" may refer to portions of a flow channel that are proximal to the most proximal fluidic compartment coupled to the channel (e.g., compartment 216), and "at or near the distal end" may refer to portions of a flow channel that are distal to the most distal fluidic compartment coupled to the channel (e.g., compartment 218).

The dimension of a flow channel exhibiting a tapering cross-sectional width can be varied as desired. For example, in certain embodiments, the cross-sectional width of the channel at or near the proximal end is approximately 80 µm, or within a range from approximately 60 µm to approximately 120 µm, and the cross-sectional width of the channel at or near the distal end is approximately 50 µm, or within a range from approximately 30 µm to approximately 70 µm. In various embodiments, the cross-sectional width at or near the proximal end is approximately 1.2 times to approximately 2 times greater than the cross-sectional width at or near the distal end, or approximately 1 time to approximately 3 times greater than the cross-sectional width near the distal end. In various embodiments, the cross-sectional width of the flow channel decreases at an average rate within a range from approximately 0.2 µm/mm to approximately 0.75 µm/mm, from approximately 0.15 µm/mm to approximately 0.3 µm/mm, from approximately 0.1 µm/mm to approximately 2 µm/mm, or from approximately 0.01 µm/mm to approximately 10 µm/mm along the length of the flow channel.

As another example, in some embodiments, some or all of the flow channels herein have a decreasing cross-sectional area along the length of the channel. For example, in certain embodiments, the cross-sectional area of the channel at or near the proximal end is approximately 2400 µm², or within a range from approximately 1200 µm² to approximately 4800 µm², and the cross-sectional area of the channel at or near the distal end is approximately 1500 µm², or within a range from approximately 600 µm² to approximately 2800 µm². In certain embodiments, the cross-sectional area of the channel at the proximal end is less than or equal to 10,000 µm². In other embodiments, the cross-sectional area of the channel at the distal end is less than or equal to 100 µm².

In alternative embodiments, some or all of the tapering flow channels herein exhibit an increasing cross-sectional dimension along the length of the channel, rather than a decreasing cross-sectional dimension. In some embodiments, the tapering profile of the cross-sectional dimension is a continuous tapering profile without discontinuities (e.g., breaks, steps, etc.). For instance, a continuous tapering profile can be a linear tapering profile that increases linearly, an exponential tapering profile that increases exponentially, a polynomial tapering profile that increases according to a polynomial function, or combinations thereof (e.g., some portions taper linearly while other portions taper exponentially, etc.). In other embodiments, the tapering profile of the cross-sectional dimension is a discontinuous tapering profile, e.g., a stepped tapering profile that increases according to a step function. Optionally, in certain embodiments, the tapering profile includes a combination of one or more portions with continuous tapering and one or more portions with discontinuous tapering.

As an example, in some embodiments, some or all of the flow channels presented herein have a increasing cross-sectional width along the length of the channel. In certain embodiments (e.g., when the cross-sectional width varies along the height of the channel), an increase in cross-sectional width is determined with respect to an average cross-sectional width, a maximum cross-sectional width, and/or a minimum cross-sectional width of the flow channel.

The dimension of a flow channel exhibiting an increasing cross-sectional width can be varied as desired. For example, in certain embodiments, the cross-sectional width of the channel at or near the distal end is approximately 80 µm, or within a range from approximately 60 µm to approximately 120 µm, or within a range from approximately 10 µm to approximately 200 µm, and the cross-sectional width of the channel at or near the proximal end is approximately 50 µm, or within a range from approximately 30 µm to approximately 70 µm, or within a range from approximately 40 µm to approximately 200 µm. In various embodiments, the cross-sectional width at or near the distal end is approximately 1.2 times to approximately 2 times greater than the cross-sectional width at or near the proximal end, or approximately 1 time to approximately 3 times greater than the cross-sectional width near the proximal end. In various embodiments, the cross-sectional width of the flow channel increases at an average rate within a range from approximately 0.2 µm/mm to approximately 0.75 µm/mm, from approximately 0.15 µm/mm to approximately 0.3 µm/mm, from approximately 0.1 µm/mm to approximately 2 µm/mm, or from approximately 0.01 µm/mm to approximately 10 µm/mm along the length of the flow channel.

As another example, in some embodiments, some or all of the flow channels herein have an increasing cross-sectional area along the length of the channel. For example, in certain embodiments, the cross-sectional area of the channel at or near the distal end is approximately 2400 µm², or within a range from approximately 1200 µm² to approximately 4800 µm², and the cross-sectional area of the channel at or near the proximal end is approximately 1500 µm², or within a range from approximately 600 µm² to approximately 2800 µm².

Constant-Diameter Flow Channels

In some embodiments, one or more flow channels of a microfluidic array have a substantially constant cross-sectional dimension (e.g., width, length, height, area) along the length of the channel, e.g., from the proximal to the distal end of the channel and/or from the proximal to the distal portion of the array. In certain embodiments, "along the length of the channel" refers to along the portion of the channel that spans the entirety of the fluidic compartments coupled to the channel. Channels exhibiting a substantially constant cross-sectional dimension along the length of the channel are also referred to herein as "constant-diameter flow channels." In some embodiments, only a subset of the flow channels of a microfluidic array are constant-diameter flow channels, such that at least some of the flow channels of the systems and devices herein do not have a substantially constant cross-sectional dimension along the length of the channel. In alternative embodiments, all of the flow channels of a microfluidic array are constant-diameter flow channels, such that each of the flow channels exhibits a substantially constant cross-sectional dimension along the length of the channel. The proportion of constant-diameter and non-constant-diameter channels in a microfluidic array can be varied as desired, e.g., such that approximately 0%, approximately 10%, approximately 20%, approximately 30%, approximately 40%, approximately 50%, approximately 60%, approximately 70%, approximately 80%, approximately 90%, or approximately 100% of the channels of the array exhibit a substantially constant cross-sectional dimension.

In some embodiments, the constant-diameter profile of the cross-sectional dimension is a continuous profile without discontinuities (e.g., breaks, steps, etc.). For instance, the profile can be substantially constant across the length of the channel. In other embodiments, the constant-diameter profile of the cross-sectional dimension is a continuous profile with discontinuities (e.g., breaks, steps, etc.), but with an average diameter that is substantially constant over the length of the channel.

Optionally, in certain embodiments, the constant-diameter profile includes a combination of one or more portions without discontinuities and one or more portions with discontinuities.

The dimension of a flow channel exhibiting a constant-diameter cross-sectional width can be selected as desired. For example, in certain embodiments, the cross-sectional width of the channel is approximately 80 µm, within a range from approximately 60 µm to approximately 120 µm, approximately 50 µm, or within a range from approximately 30 µm to approximately 70 µm. In some embodiments, the cross-sectional width of the channel is within a range from approximately 40 µm to approximately 200 µm, or within a range from approximately 10 µm to approximately 200 µm. In some embodiments, the flow channels have cross-sectional areas of approximately 2400 µm$^2$, within a range from approximately 1200 µm$^2$ to approximately 4800 µm$^2$, 1500 µm$^2$, within a range from approximately 600 µm$^2$ to approximately 2800 µm$^2$, or within a range from approximately 100 µm$^2$ to approximately 10,000 µm$^2$.

Microfluidic Devices for Self-Digitization of Fluidic Samples

In some embodiments, the present disclosure provides a microfluidic device (e.g., a microfluidic chip) having one or more microfluidic arrays for discretizing one or more fluidic samples into a plurality of fluidic compartments. In certain embodiments, a microfluidic device includes 2, 4, 6, 8, 12, 16, 24, 32, 36, or 48 microfluidic arrays and/or at least 500, at least 1000, at least 5000, at least 10,000, at least 50,000, at least 100,000, at least 500,000, at least 1 million, at least 5 million, or at least 10 million fluidic compartments.

In some embodiments, the microfluidic devices of the present disclosure are configured for centrifugal loading of fluidic samples. In such embodiments, the microfluidic device includes a device body with a proximal body portion configured to be oriented towards the axis of rotation during centrifugation, and a distal body portion configured to be oriented away from the axis of rotation during centrifugation. Accordingly, the one or more microfluidic arrays are formed in the body of the microfluidic device with the flow channels (e.g., parallel flow channels) extending from the proximal body portion to the distal body portion, such that centrifugation drives fluid through the arrays from the proximal ends of the flow channels to the distal ends of the flow channels. The plurality of microfluidic arrays can be formed in the device body in a variety of ways, such as 3D printing, replica molding, injection molding, embossing, soft lithography, or a combination thereof.

FIGS. 3A and 3B illustrate a microfluidic device 300 for self-digitization of fluidic samples, in accordance with embodiments. Similar to the device 100 of FIG. 1, the device 300 includes a plurality of microfluidic arrays each having at least one fluid inlet port 302, one or more flow channels 304, a plurality of fluidic compartments 306, and at least one fluid outlet port 308. In some embodiments, the fluid inlet port(s) 302 are coupled to the flow channels 304 via an optional inlet reservoir 310 and a branching channel 312, and the fluid outlet port(s) 308 are coupled to the flow channels 304 via an optional outlet reservoir 314 and outlet return channel 316. Optionally, the fluidic compartments 306 each include a respective drainage channel 318 coupled to the respective flow channel 304.

In some embodiments, the body of the device 300 is formed from a polydimethylsiloxane (PDMS) layer 320 on a glass slide 322 with a spin-coated PDMS layer 324. The features of the microfluidic arrays (e.g., flow channels 304, fluidic compartments 306) are formed in the PDMS layer 320 in accordance with methods known to one of ordinary skill in the art. In certain embodiments, a first PDMS block 326 is used to form the outlet reservoir 314 and a second PDMS block 328 is used to form the inlet and outlet ports 302, 308 and inlet reservoir 310. In some embodiments, the first and/or second PDMS blocks 326, 328 are separate from the PDMS layer 320, while in other embodiments, the first and/or second PDMS blocks 326, 328 are integrally formed as a single piece with the PDMS layer 320. Optionally, a vapor barrier 330 is positioned over the PDMS layer 320, e.g., to reduce evaporation of fluid through the PDMS layer 320.

The depths of the features formed in the device using PDMS can be varied as desired. For instance, in certain embodiments, the fluid inlet port(s) 302, fluid outlet port(s) 308, inlet reservoir 310, and/or outlet reservoir 314 have a depth of at least approximately 0.05 mm, 0.1 mm, 0.2 mm, 0.5 mm, 1 mm, 2 mm, 3 mm, 4 mm, 5 mm, or 6 mm.

The microfluidic devices of the present disclosure can be designed in a variety of ways. For example, in some embodiments, the body of a microfluidic device comprises a substantially rectangular shape, a substantially square shape, a substantially circular shape, a substantially semi-circular shape, a substantially oval shape, a substantially semi-oval shape, or any other geometry. In certain embodiments, the body of a microfluidic device is shaped to be similar to existing devices and/or accommodate existing instrumentation, e.g., for convenience and compatibility. For instance, in various embodiments, the body is substantially rectangular with a length (e.g., along the proximal-distal direction) of approximately 127.8 mm and a width (e.g., orthogonal to the proximal-distal direction) of approximately 85.5 mm, similar to a 96-well microplate. As another example, in various embodiments, the body is substantially rectangular with a length of approximately 100 mm and a width of approximately 75 mm, similar to the adapter size for certain PCR thermal cycling devices.

In some embodiments, the arrangement of the microfluidic arrays in the body of the microfluidic device is configured to be compatible with existing laboratory equipment, such as a multi-channel pipette. For instance, some embodiments of the present disclosure provide microfluidic devices configured for sample loading using a multi-channel pipette.

In various embodiments, a multi-channel pipette is used to concurrently load a plurality of fluidic samples into a plurality of fluid inlet ports of a microfluidic device, with each fluid inlet port receiving a different fluidic sample from a respective channel of the pipette. In certain embodiments, each fluid inlet port is fluidly coupled to a different microfluidic array, such that the different fluidic samples can be discretized in parallel in accordance with the methods presented herein. This approach allows for simultaneous discretization of multiple samples using a single microfluidic device and is advantageous for high-throughput sample processing.

Accordingly, in some embodiments, the fluid inlet ports of the microfluidic arrays formed in a microfluidic device are arranged to receive fluidic samples from a multi-channel pipette. In certain embodiments, for example, the fluid inlet ports are arranged in a linear row (e.g., near the proximal body portion of the device) similar to the arrangement of pipette channels of a multi-channel pipette. In certain embodiments, the number of fluid inlet ports and pitch (e.g., center-to-center distance) between adjacent fluid ports corresponds to the number of channels and channel pitch of a multi-channel pipette, respectively. For instance, in various embodiments, a multi-channel pipette includes 4, 6, 8, or 12 pipette channels, with the pitch between adjacent pipette channels being approximately 2.25 mm, 3 mm, 4.5 mm, 9 mm, 12 mm, 18 mm, or 36 mm. Accordingly, in various embodiments, the microfluidic device has 4, 6, 8, or 12 fluid inlet ports, with the pitch between adjacent ports being approximately 2.25 mm, 3 mm, 4.5 mm, 9 mm, 12 mm, 18 mm, or 36 mm.

Figure 4A:
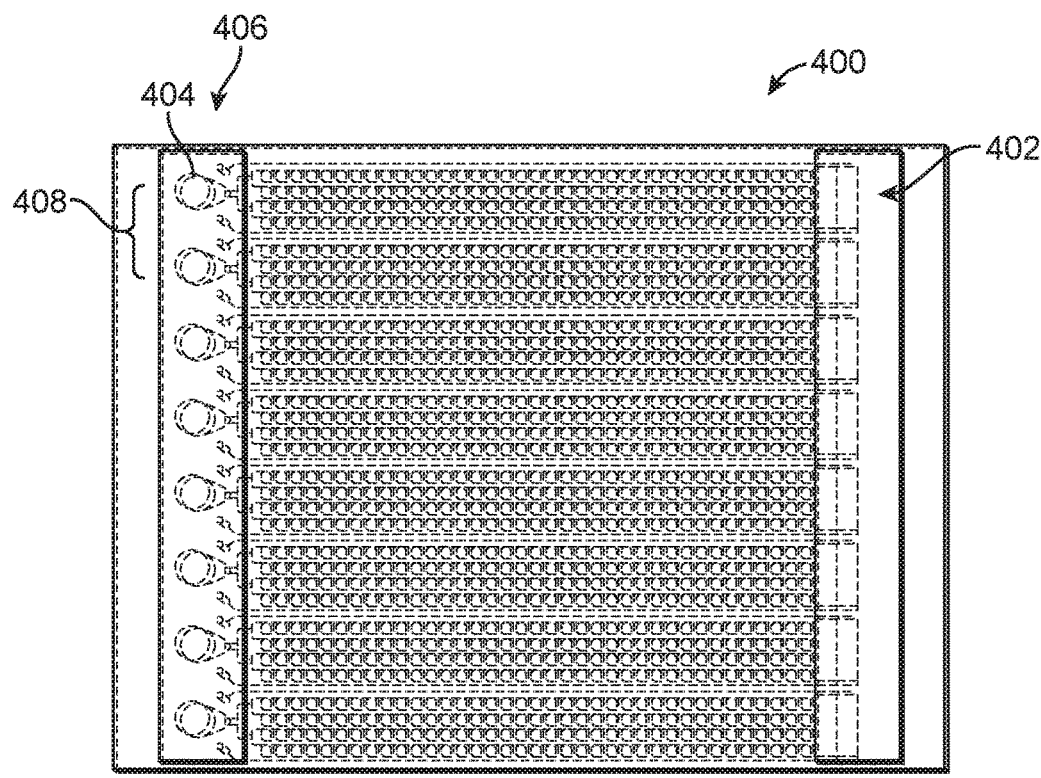
FIGS. 4A and 4B illustrate microfluidic devices configured for use with multi-channel pipettes.

FIG. 4A illustrates an exemplary microfluidic device 400 configured for use with multi-channel pipettes, in accordance with embodiments The device 400 includes 8 microfluidic arrays 402 each having a single fluid inlet port 404 for sample loading. Each fluid inlet port 404 is fluidly coupled to a plurality of flow channels (e.g., 4 flow channels) and fluidic compartments (e.g., 148 fluidic compartments), similar to various embodiments presented herein. The 8 fluid inlet ports 404 are arranged in a linear row at the proximal portion 406 of the device 400. In some embodiments, the pitch 408 between adjacent fluid inlet ports is approximately 9 mm in order to accommodate a standard 8-channel pipette.

Figure 4B:
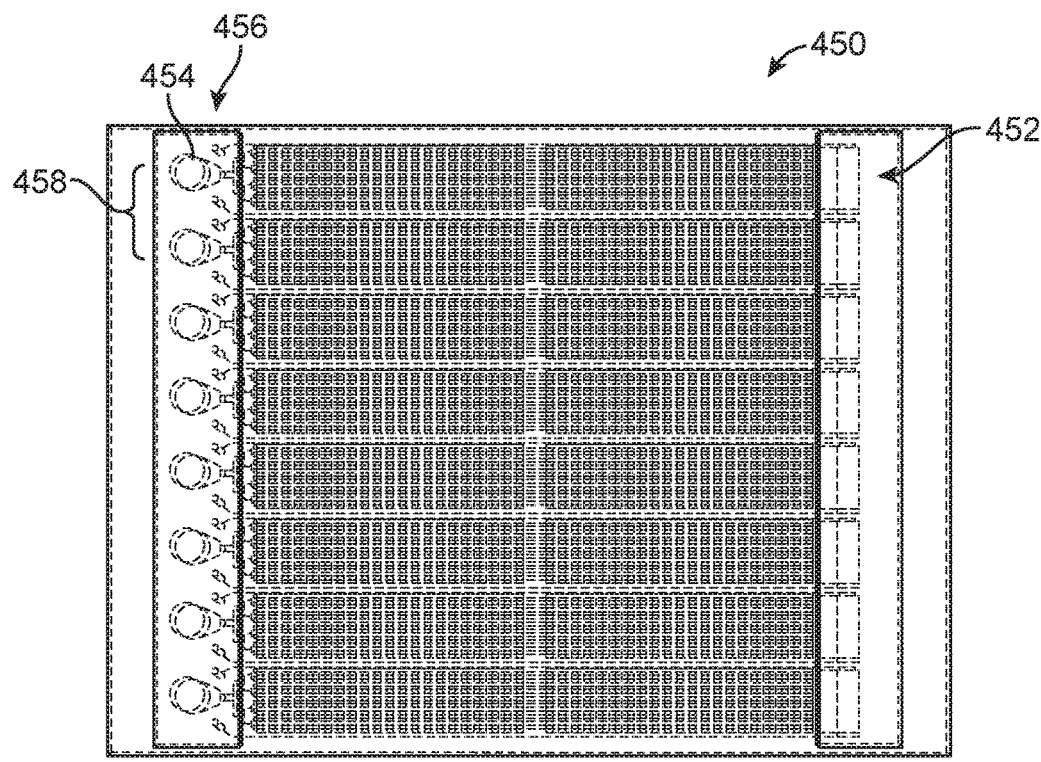

FIG. 4B illustrates another exemplary microfluidic device 450 configured for use with multi-channel pipettes, in accordance with embodiments. Similar to the device 400, the device 450 includes 8 microfluidic arrays 452 each having a single fluid inlet port 454 for sample loading. Each fluid inlet port 454 is fluidly coupled to a plurality of flow channels (e.g., 16 flow channels) and fluidic compartments (e.g., 2560 fluidic compartments). The 8 fluid inlet ports 454 are arranged in a linear row at the proximal portion 456 of the device 400. In some embodiments, the pitch 458 between adjacent fluid inlet ports is approximately 9 mm in order to accommodate a standard 8-channel pipette.

In certain embodiments, the number of channels of the pipette matches the number of fluid inlet ports and the channel pitch matches the port pitch, such that there is a one-to-one correspondence between channels of the multi-channel pipette and fluid inlet ports of the microfluidic device. In such embodiments, a single pipette may be used to concurrently load samples into all of the fluid inlet ports at once, e.g., an 8-channel pipette having a 9 mm pitch is used to load samples into a device with 8 fluid inlet ports having a 9 mm pitch, a 12-channel pipette having a 4.5 mm pitch is used to load samples into a device with 12 fluid inlet ports having a 4.5 mm pitch, etc.

In alternative embodiments, the number of channels of the pipette differs from the number of fluid inlet ports, and/or the channel pitch differs from the port pitch, such that there is not a one-to-one correspondence between the pipette channels and the fluid inlet ports. Optionally, the number of ports is a multiple of the number of channels and/or the port pitch is a multiple of the channel pitch. In such embodiments, multiple sequential loading steps can be used to load sample into the fluid inlet ports, e.g., an 8-channel pipette having a 9 mm pitch is used to load samples into a device with 16 fluid inlet ports having a 4.5 mm pitch by first loading the odd ports, then the even ports (or vice-versa).

In some embodiments, a microfluidic device comprises a plurality of fluid inlet ports with one or more of the following configurations: 2 fluid inlet ports with a pitch of approximately 36 mm, 4 fluid inlet ports with a pitch of approximately 18 mm, 6 fluid inlet ports with a pitch of approximately 12 mm, 8 fluid inlet ports with a pitch of approximately 9 mm, 12 fluid inlet ports with a pitch of approximately 9 mm, 16 fluid inlet ports with a pitch of approximately 4.5 mm, 24 fluid inlet ports with a pitch of approximately 4.5 mm, 24 fluid inlet ports with a pitch of approximately 3 mm, 36 fluid inlet ports with a pitch of approximately 3 mm, 32 fluid inlet ports with a pitch of approximately 2.25 mm, or 48 fluid inlet ports with a pitch of approximately 2.25 mm.

Materials and Compositions for Self-Digitization of Fluidic Samples

The microfluidic arrays and devices of the present disclosure can be fabricated from a wide variety of materials. For instance, in some embodiments, the devices herein, or one or more components thereof, comprise a material selected from the following: polydimethylsiloxane (PDMS), polypropylene (PP), polychlorotrifluoroethylene (PCTFE), thermoset polyester (TPE), polymethylmethacrylate (PMMA), polyurethane methacrylate, polyethylene, polyester (PET), polytetrafluoroethylene (PTFE), polycarbonate, parylene, polyvinyl chloride, fluoroethylpropylene, lexan, polystyrene, cyclic olefin polymers (COP), cyclic olefin copolymers, polyurethane, polyurethane blended with polyacrylate, polyestercarbonate, polypropylene, polybutylene, polyacrylate, polycaprolactone, polyketone, polyphthalamide, cellulose acetate, polyacrylonitrile, polysulfone, an epoxy polymer, a thermoplastic, a fluoropolymer, polyvinylidene fluoride, polyamide, polyimide, glass, quartz, silicon, a gallium arsenide, a silicon nitride, fused silica, ceramic, metal, or a combination thereof. Optionally, in various embodiments (e.g., for biological assays), a device is fabricated from a polymer material so the device is disposable for one-time use.

In some embodiments, the devices of the present disclosure comprise a material with suitable surface properties to facilitate the digitization process. The surface properties of the devices or device components (e.g., channels and/or fluidic compartments) can be tailored for a specific application. For example, some or all surfaces of the devices are hydrophobic or hydrophilic in certain embodiments. In some embodiments, certain surfaces are hydrophobic and certain surfaces are hydrophilic. In some embodiments, the surfaces that are hydrophilic or hydrophobic are designed so as to allow loading of oils in certain channels and/or fluidic compartments and aqueous solutions in certain channels and/or fluidic compartments in the device.

For instance, in certain embodiments, one or more portions of a microfluidic device (e.g., flow channel, fluidic compartments, device body, etc.) comprise a hydrophobic surface and/or are fabricated from a hydrophobic material, such as natively hydrophobic or surface-treated polydimethylsiloxane (PDMS), polycarbonate (PC), polypropylene (PP), glycol modified polyethylene terephthalate (PETG), cyclic olefin copolymer (COC), cyclic olefin polymer (COP), polychlorotrifluoroethylene (PCTFE), a multilaminate material, or a combination thereof.

In some embodiments, one or more portions of a microfluidic device (e.g., all of the flow channels and/or the plurality of fluidic compartments) are modified with chemical and/or biological reagents to render the surfaces in contact with fluids preferential for wetting by a selected fluid (e.g., an oil). In certain embodiments, wetting primes the surface of the device for discretization by facilitating displacement of certain types of fluids from the device surfaces (e.g., oils) and/or resisting displacement of certain types of fluids from the device surfaces (e.g., aqueous solutions).

A diverse variety of fluids or liquids can be used with the various devices, systems and methods of the present disclosure. In some embodiments, the fluids include water-based or aqueous solutions, for example. In some embodiments, the fluids include liquids that are sparingly soluble in aqueous solutions, such as oils (e.g., fluorinated oils, hydrocarbon oils, silicone oils, or mineral oils). Optionally, organic solvents are also used.

In certain embodiments, a fluid used with the devices, systems, and methods herein comprises a fluidic sample (e.g., an aqueous solution) containing a variety of analytes, e.g., including but are not limited to: chemicals, biochemicals, genetic materials (e.g., DNA, RNA, etc.), expressed products of genetic materials (e.g., proteins and/or metabolites), crystallizing molecules, biological cells, exosomes, mitochondria, drugs, biological particles that circulate in peripheral blood or lymphatic systems, rare cells, particle, or combinations thereof. Possible aqueous fluidic samples include but are not limited to: various PCR and RT-PCR solutions, isothermal amplification solutions such as for LAMP or NASBA, blood samples, plasma samples, serum samples, solutions that contain cell lysates or secretions or bacterial lysates or secretions, and other biological samples containing proteins, bacteria, viral particles and/or cells (eukaryotic, prokaryotic, or particles thereof), among others. In certain embodiments, the fluidic sample also contains surfactants or other agents to facilitate desired interactions and/or compatibility with immiscible fluids (e.g., the first/third fluid) and/or the material of the device. In certain embodiments, the fluidic sample includes one or more of: cells expressing a malignant phenotype, fetal cells, circulating endothelial cells, tumor cells, cells infected with a virus, cells transfected with a gene of interest, or T-cells or B-cells present in the peripheral blood of subjects afflicted with autoimmune or autoreactive disorders, or other subtypes of immune cells, or rare cells or biological particles (e.g., exosomes, mitochondria) that circulate in peripheral blood or in the lymphatic system or spinal fluids or other body fluids. The cells or biological particles are optionally rare in a sample, such that the discretization is used to spatially isolate the cells thereby allowing for detection of the rare cells or biological particles, for example.

In some embodiments, the devices of the present disclosure function as at least a two-phase system, utilizing two or more immiscible fluids. For example, in some embodiments, a first fluid (e.g., an oil phase) is used to initially fill a device to displace any air. In some embodiments, the first fluid is configured to preferentially wet the device surface relative to a second fluid. Subsequently, in some embodiments, the second fluid, which is typically immiscible with the first fluid (e.g., an aqueous fluidic sample containing the sample of interest) is flowed through the device and enters the fluidic compartments, displacing the oil. Optionally, a third fluid is then flowed through the device to displace the aqueous phase within the main flow channels but not the fluidic compartments. The third fluid is typically immiscible with the second fluid, and may or may not be the same as the first fluid, and may or may not be miscible with the first fluid. In certain embodiments, the fluidic compartments serve as shelters to isolate and digitize individual fluidic packets of the aqueous phase within the fluidic compartments. Optionally, the fluidic compartments are substantially occupied by the aqueous phase such that the fluidic packets assume substantially the shape of the fluidic compartment and the volume of the fluidic packet is substantially defined by the dimensions of the compartment. For example, if a fluidic compartment is rectangular shaped, the fluidic packet contained within, can substantially assume a rectangular shape.

In certain embodiments, the first and/or third fluids each comprise an oil, such as a fluorinated oil, a hydrocarbon oil, a silicone oil, or a combination thereof. In some embodiments, the oil used as the first and/or third fluid is a mineral oil-based oil, fluorocarbon-based oil, and/or silicone oil-based oil. Other embodiments can use other "oil" phases or alternative materials. In certain embodiments, the first and/or third fluid also includes a surfactant and/or wetting agent to improve desired interaction with the device surface and/or with the second fluid. In some embodiments, the first and the third fluid are identical, while in other embodiments, the first and third fluid are composed of the same base material, but have different surfactant/additive concentrations and/or compositions. In yet other embodiments, the third fluid is of a completely different composition than the first fluid and may or may not be miscible with the first fluid. In certain embodiments, the first and/or third fluid contain components that interact with the second fluid and/or components within the second fluid. When a plurality of oils are used in a given method of operation (e.g., the first fluid, the third fluid, and/or the fourth fluid), the compositions of the oils can be the same or different. In some embodiments, each of the oil compositions is independently selected regardless of the composition of the other oils in use.

In some embodiments, the second fluid comprises a fluidic sample containing one or more analytes of interest. The second fluid is optionally an aqueous solution. Examples of aqueous solutions include but are not limited to: various PCR and RT-PCR solutions, isothermal amplification solutions such as for LAMP or NASBA, blood samples, plasma samples, serum samples, solutions that contain cell lysates or secretions or bacterial lysates or secretions, and other biological samples containing proteins, bacteria, viral particles and/or cells (eukaryotic, prokaryotic, or particles thereof), or combinations thereof.

In some embodiments, a fourth fluid is provided. In certain embodiments, the fourth fluid comprises an oil, such as a fluorinated oil, a hydrocarbon oil, a silicone oil, or a combination thereof. In some embodiments, the fourth fluid comprises a fluid that is compatible with an amplification reaction, such as PCR or isothermal amplification. For instance, in certain embodiments, the fourth fluid is used to displace the third fluid in the flow channel before beginning an amplification reaction to amplify a digitized analyte. The fourth fluid may be miscible or immiscible with any of the first, second, and/or the third fluids. Optionally, in certain embodiments, the fourth fluid is the same as the first fluid.

In some embodiments, a fifth fluid is provided. In certain embodiments, the fifth fluid comprises an oil, such as a fluorinated oil, a hydrocarbon oil, a silicone oil, or a combination thereof. In certain embodiments, the fifth fluid is used to flush the first, second, third, and/or fourth fluids from the device.

In some embodiments, any of the fluids herein (e.g., first, second, third, fourth, and/or fifth fluids) are provided to a fluid inlet port on the microfluidic device. The fluids may be provided to the same fluid inlet port or to different fluid inlet ports. In certain embodiments, the first, second, third, fourth, and/or fifth fluids discussed herein are provided to a device in a sequential order that is different from the sequential orders provided herein. The first, second, third, fourth, and/or fifth fluids can be provided to a device in any order, and any of the first, second, third, fourth, and/or fifth fluids may be omitted in some embodiments of the present disclosure. The sequential orders described herein are exemplary and non-limiting to the practice of the disclosed methods.

In various embodiments, the present disclosure provides methods for introducing a fluid into a microfluidic device, the method comprising: providing a microfluidic device according to the present disclosure; and introducing a first fluid into the flow channel of the microfluidic device. The terms "providing" and "introducing" are used interchangeably herein to refer to the movement of fluid into or through a structure, such as for example an inlet or a channel.

In various embodiments, the present disclosure provides methods for introducing a fluid into a microfluidic device, the method comprising: providing a microfluidic device according to the present disclosure; and introducing a second fluid into the flow channel of the microfluidic device, wherein the second fluid is an aqueous solution.

In some embodiments, the second fluid comprises a fluidic sample comprising an analyte and the method further comprises performing an analysis of the analyte within at least one of the fluidic compartments. In certain embodiments, the analyte comprises a biological material. In further embodiments, the biological material is selected from a cell, a bacteria, a virus, a prion, a nucleic acid, a protein, an expressed product of a genetic material, a crystallizing molecule, a particle, or a combination thereof. In yet further embodiments, the second fluid comprises a first nucleic acid molecule and a second nucleic acid molecule and the method further comprises distributing the first nucleic acid molecule into a first fluidic compartment, wherein the first fluidic compartment does not comprise the second nucleic acid molecule.

In some embodiments, the present methods further comprise introducing a first fluid into the flow channel of the microfluidic device, wherein the first fluid is introduced into the flow channel before the second fluid is introduced into the flow channel. In some embodiments, the first fluid comprises an oil. In further embodiments, the oil is selected from a fluorinated oil, a hydrocarbon oil, a silicone oil, or a combination thereof.

In some embodiments, the methods further comprise introducing a third fluid into the flow channel of the microfluidic device. In certain embodiments, the third fluid is introduced into the flow channel after the second fluid is introduced into the flow channel. In other embodiments, the first fluid is an oil, the second fluid is an aqueous solution, and the third fluid is an oil.

In some embodiments, the methods further comprise introducing a fourth fluid into the flow channel of the microfluidic device. In certain embodiments, the fourth fluid is introduced into the flow channel after the first fluid is introduced into the flow channel and before the second fluid is introduced into the flow channel. In other embodiments, the fourth fluid is introduced into the flow channel after the second fluid is introduced into the flow channel and before the third fluid is introduced into the flow channel. In some embodiments, the fourth fluid is introduced into the flow channel after the third fluid is introduced into the flow channel. In further embodiments, the first fluid is an oil, the second fluid is an aqueous solution, the third fluid is an oil, the fourth fluid is an oil, and the fifth fluid is an oil, and wherein the first, third, fourth, and fifth fluids are independently the same or different from one another. In yet further embodiments, each of the oils are independently selected from a fluorinated oil, a hydrocarbon oil, a silicone oil, or a combination thereof.

In some embodiments, the methods further comprise introducing a fifth fluid into the flow channel of the microfluidic device. In certain embodiments, the fifth fluid is introduced into the flow channel after the second fluid is introduced into the flow channel. In other embodiments, the fifth fluid is introduced into the flow channel after the third fluid is introduced into the flow channel. In some embodiments, the method further comprises introducing a fourth fluid into the flow channel, wherein the fourth fluid is introduced into the flow channel after the first fluid is introduced into the flow channel and before the second fluid is introduced into the flow channel. In certain embodiments, the first fluid is an oil, the second fluid is an aqueous solution, the third fluid is an oil, the fourth fluid is an oil, and the fifth fluid is an oil, and wherein the first, third, fourth, and fifth fluids are independently the same or different from one another. In further embodiments, each of the oils are independently selected from a fluorinated oil, a hydrocarbon oil, a silicone oil, or a combination thereof.

Systems for Self-Digitization, Processing, and Analysis of Fluidic Samples

Various embodiments of the present disclosure provide systems for self-digitization, processing, and/or analysis of fluidic samples. In some embodiments, a system is configured to discretize a fluidic sample by driving fluid into the fluidic compartments of a microfluidic device by centrifugation. In certain embodiments, the system configured for discretizing a plurality of fluidic samples includes a rotor assembly configured to receive one or more microfluidic devices, and a rotary actuator configured to rotate the rotor assembly about an axis of rotation (e.g., a central axis of the rotor assembly) in order to generate centrifugal forces for driving fluid into the fluidic compartments of the microfluidic device(s). The systems herein advantageously provide a simple and convenient format for simultaneous discretization of multiple fluidic samples suitable for high-throughput processing and analysis.

A rotor assembly for self-digitization of fluidic samples can be configured in a variety of ways. In some embodiments, a rotor assembly includes a central axis and a plurality of receptacles arranged radially around the central axis. The rotor assembly can include any number of receptacles, such as 2, 3, 4, 5, 6, 7, 8, 9, 10, 11, 12, or more receptacles. The distance between the proximal end of each of the plurality of receptacles and the central axis is within a range from about 10 mm to about 500 mm, from about 20 mm to about 300 mm, or from about 30 mm to about 200 mm, in some embodiments. The receptacles are each shaped to receive one or more microfluidic devices of the present disclosure. For instance, in various embodiments, a receptacle is sized and/or shaped to substantially match the size and/or shape of a device body of a microfluidic device (e.g., has a length of approximately 127.8 mm and a width of approximately 85.5 mm, or a length of approximately 100 mm and a width of approximately 75 mm). In certain embodiments, the receptacles are shaped to removably receive and couple to the microfluidic devices, e.g., via interference fits, snap fits, fasteners, latches, clamps, or other suitable coupling mechanisms.

In some embodiments, the receptacles are arranged such that the proximal body portion of a received microfluidic device is positioned near the central axis of the rotor assembly, while the distal body portion of the device is positioned away from the central axis of the rotor assembly. Accordingly, in such embodiments, rotation of the rotor assembly causes fluid to be driven through the device from the proximal portion to the distal portion. As discussed above and herein, the microfluidic device optionally includes tapering flow channels with a decreasing cross-sectional dimension from the proximal portion to the distal portion in order to promote uniform fluid flow during centrifugation.

The rotary actuator can be any actuation mechanism suitable for rotating the rotor assembly about an axis of rotation, such as a brushless direct current motor, a brushed direct current motor, a servo motor, or a stepper motor. In certain embodiments, the rotary actuator is configured to rotate the rotor assembly at approximately 10 RPM, 50 RPM, 100 RPM, 200 RPM, 300 RPM, 400 RPM, 500 RPM, 600 RPM, 700 RPM, 800 RPM, 900 RPM, 1000 RPM, 1500 RPM, 2000 RPM, 2500 RPM, 3000 RPM, 3500 RPM, 4000 RPM, 4500 RPM, or 5000 RPM. In various embodiments, the rotational speed of the rotary actuator is configured for driving fluid through the microfluidic devices in order to discretize fluidic samples. Optionally, the rotational speed is configured for other applications, such as the imaging procedures discussed further herein. In certain embodiments, the rotation of the rotary actuator is controlled by one or more processors configured with instructions for controlling the operation of the self-digitization system, as discussed further herein.

Figure 5:
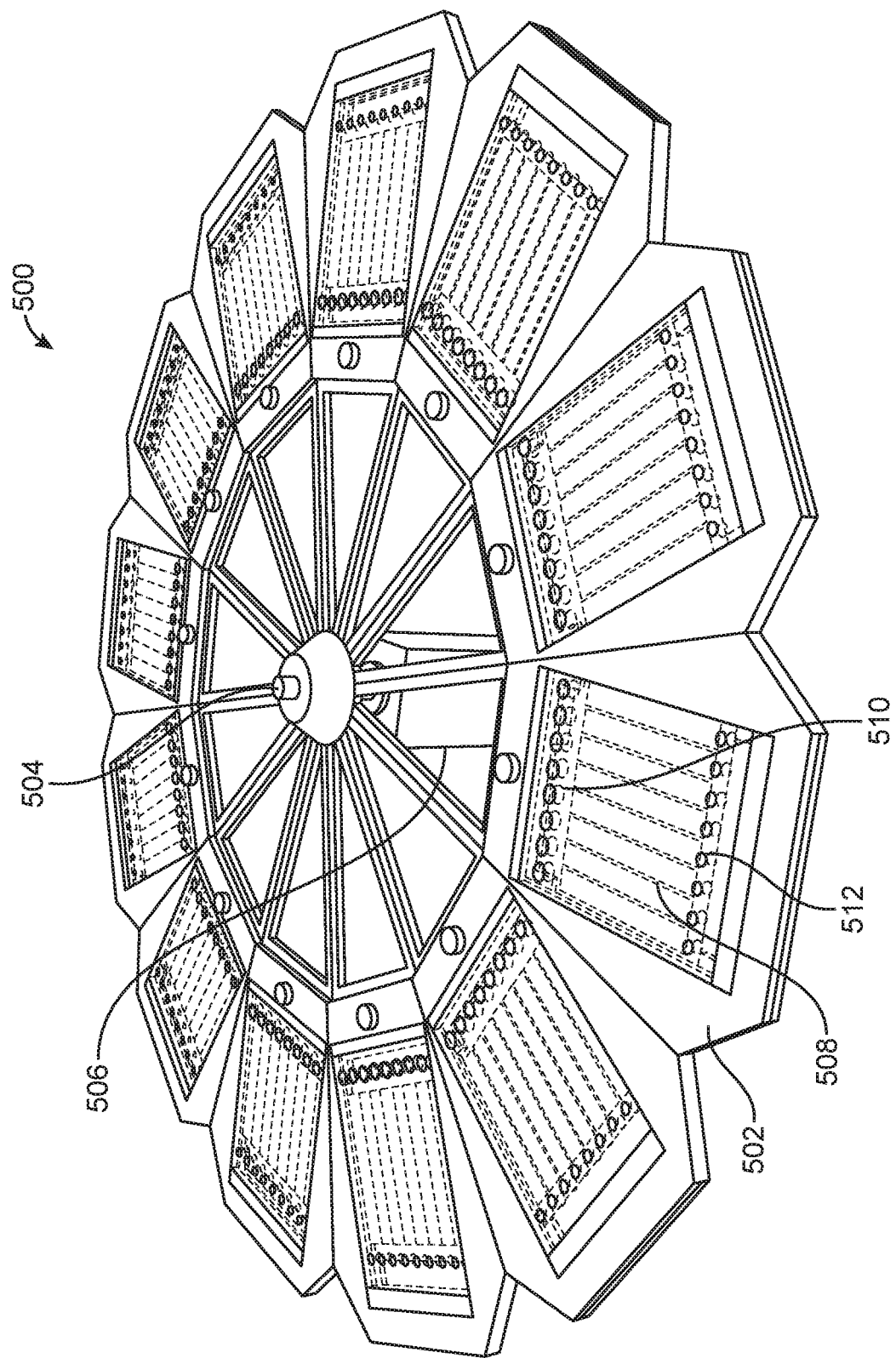
FIG. 5 illustrates a rotor assembly of a system for self-digitization of fluidic samples.

FIG. 5 illustrates a rotor assembly 500 of a system for self-digitization of fluidic samples, in accordance with embodiments. The rotor assembly 500 includes a plurality of receptacles 502 (e.g., 12 receptacles) arranged radially about a central axis 504. The central axis 504 is coupled to a rotary actuator 506, depicted herein as being positioned underneath the rotor assembly 500. Each receptacle 502 is shaped to receive a corresponding microfluidic device 508. The microfluidic devices 508 can be similar to any embodiment of the devices discussed herein, such as the device 300, 400, or 450. In certain embodiments, the devices 508 are positioned in their corresponding receptacles 508 such that the proximal portion 510 of the device 508 is oriented towards the central axis 504 and the distal portion 512 of the device 508 is oriented away from the central axis 504. As discussed above and herein, in some embodiments, the fluid inlet ports and fluid outlet ports of the device 508 are located at the proximal portion 510, the outlet reservoir is located at the distal portion 512, and the flow channels extend from the proximal portion 510 to the distal portion 512.

In some embodiments, a rotor assembly is integrally formed as a single piece such that the receptacles cannot be decoupled from each other without damaging the assembly. In such embodiments, the number of receptacles is fixed. In alternative embodiments, the rotor assembly includes removably coupled receptacles such that the number of receptacles can be adjusted according to user preference. Removably coupled receptacles can be attached to the rotor assembly in a variety of ways, including but not limited to fasteners (e.g., screws, pins), interlocking elements, snap fits, interference fits, latches, clamps, and the like.

Figure 6A:
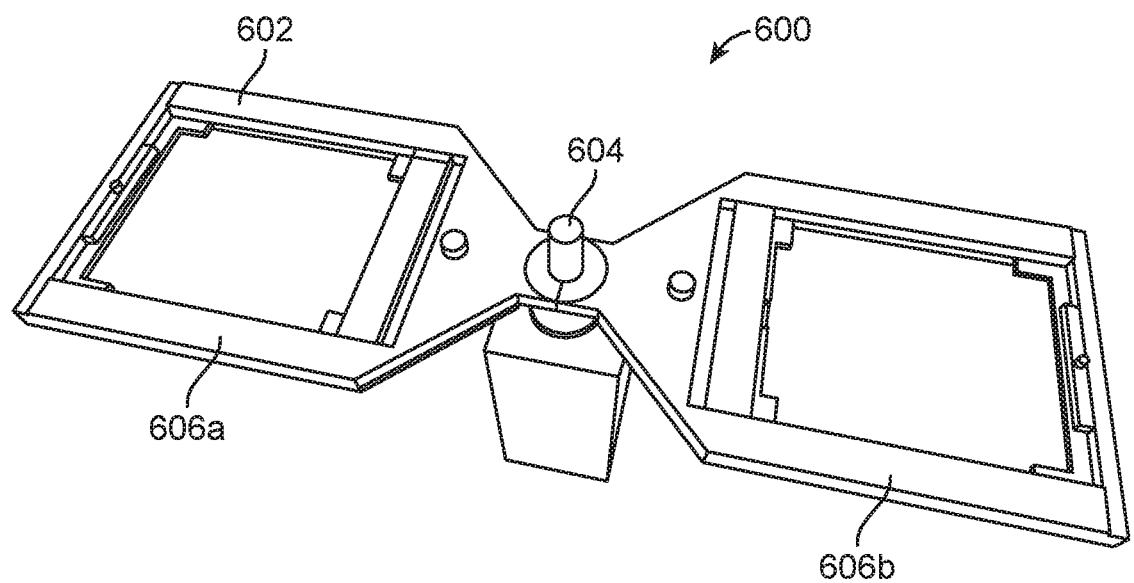
FIGS. 6A and 6B illustrate first and second configurations of a rotor assembly with removably coupled receptacles, respectively.
Figure 6B:
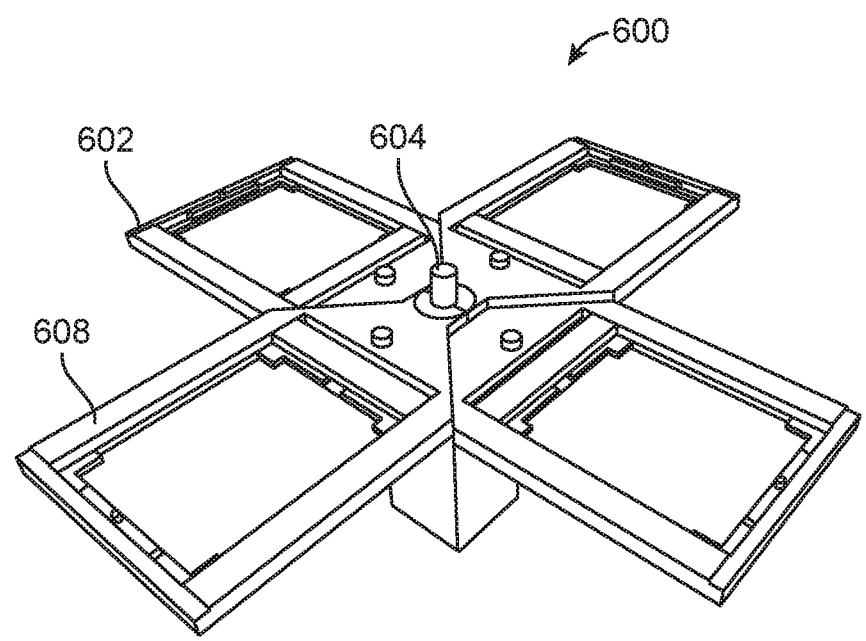

FIGS. 6A and 6B illustrate a rotor assembly 600 with removably coupled receptacles, in accordance with embodiments. FIG. 6A illustrates a first configuration of the rotor assembly 600 in which a first removable rotor component 602 is coupled to the central axis 604 of the assembly 600. In the depicted embodiment, the rotor component 602 includes a pair of receptacles 606a, 606b positioned opposite each other. Accordingly, the first configuration is suitable for spinning two microfluidic devices simultaneously. FIG. 6B illustrates a second configuration of the rotor assembly 600 in which a first removable rotor component 602 and a second removable rotor component 608 are coupled to the central axis 604, e.g., orthogonal to each other. The second removable rotor component 608 is substantially similar to the first removable rotor component 602. Accordingly, the second configuration is suitable for spinning four microfluidic devices simultaneously.

Various embodiments of the present disclosure provide systems and devices configured to perform other functionalities in addition to self-digitization of fluidic samples via centrifugation. In some embodiments, a system for self-digitization as discussed herein also incorporates components configured to perform one or more of the following functions: heating of one or more fluidic samples in a microfluidic device, cooling of one or more fluidic samples in a microfluidic device, measuring a property of one or more fluidic samples in a microfluidic device, and/or imaging one or more fluidic samples in a microfluidic device. For instance, various embodiments of the systems herein are configured to perform discretization, thermal cycling, and imaging of a plurality of fluidic samples, e.g., for dPCR applications. Such multifunctional systems provide a convenient and compact unified platform for high-throughput discretization, processing, and analysis of fluidic samples.

For instance, in some embodiments, a multifunctional system for sample discretization, processing, and analysis further includes one or more heating devices configured to generate and apply heat to the fluidic samples contained within the microfluidic devices received in the rotary actuator. The heating devices can include a Peltier device, a convection heater, radiation-emitting heater, a resistive heater, an inductive heater, or a combination thereof. The heating devices can be configured to apply heat with or without directly contacting the microfluidic devices, as desired. In certain embodiments, application of heat to the microfluidic devices is controlled by one or more processors configured with instructions for controlling the operation of the self-digitization system, as discussed further herein.

As another example, in some embodiments, the systems herein further include one or more cooling devices for reducing the temperature of the fluidic samples contained within the microfluidic devices received in the rotary actuator. The cooling devices can include a Peltier device, a convection cooling device, or a combination thereof. The cooling devices can be configured to apply cooling with or without directly contacting the microfluidic devices, as desired. In certain embodiments, application of cooling to the microfluidic devices is controlled by one or more processors configured with instructions for controlling the operation of the self-digitization system, as discussed further herein.

Figure 7B:
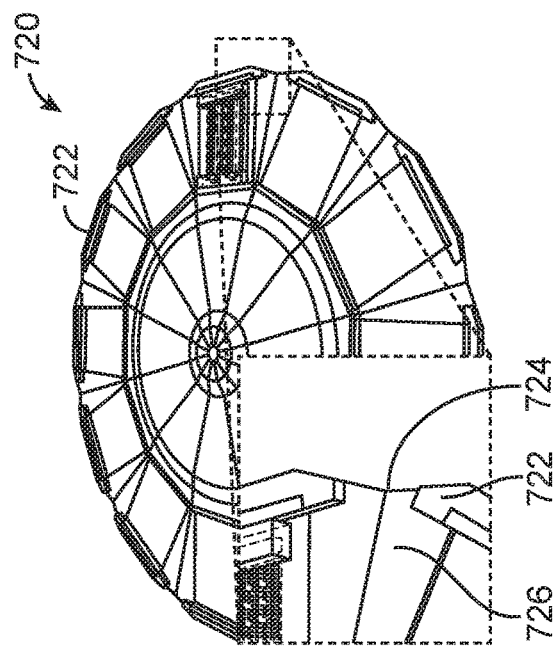
FIGS. 7A through 7C illustrate rotor assemblies configured to accommodate heating and/or cooling of microfluidic devices.
Figure 7C:
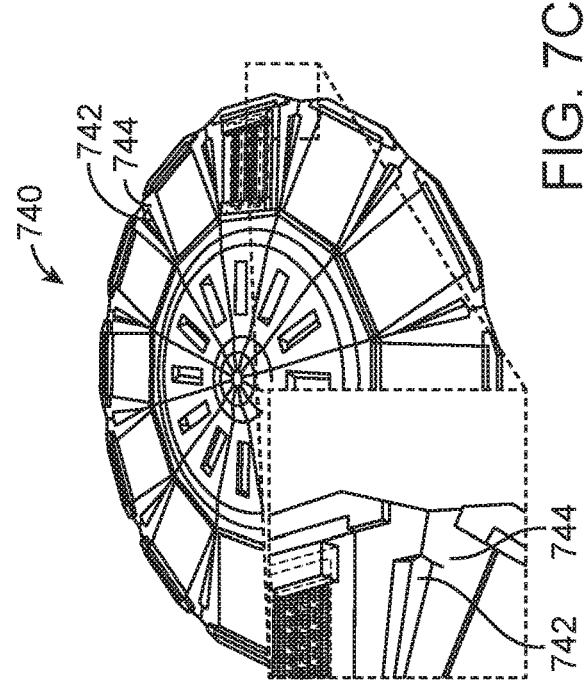
Figure 7A:
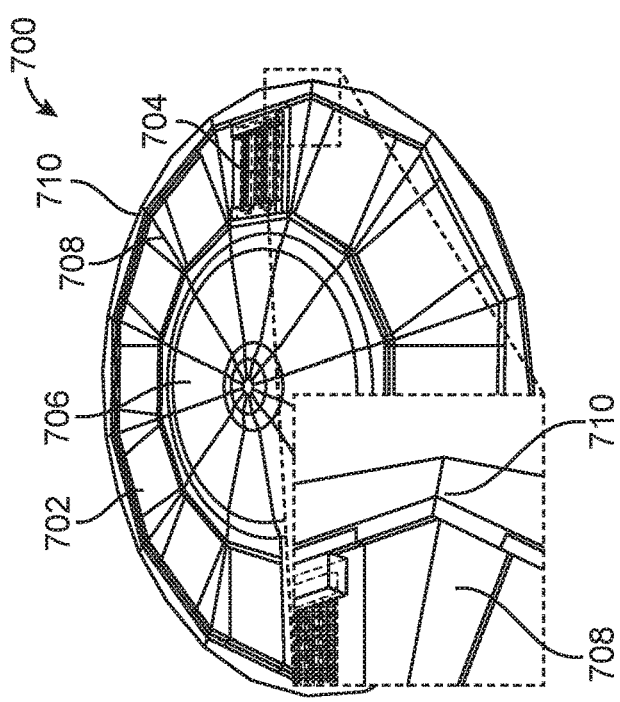

FIGS. 7A through 7C illustrate exemplary rotor assemblies configured to accommodate heating and/or cooling of microfluidic devices (e.g., via convective heating and/or cooling), in accordance with embodiments. FIG. 7A illustrates a rotor assembly 700 with a plurality of receptacles 702 (e.g., 12 receptacles) for receiving microfluidic devices (e.g., device 704). Each receptacle 702 includes an opening shaped to receive the device and to expose the bottom surface of the device for thermal coupling to a heating device and/or cooling device. In some embodiments, the rotor assembly includes an inner portion 706, middle portion 708, and outer portion 710 spanning the entire perimeter of the rotor assembly 700. The inner portion 706 and outer portion 710 are relatively thick, e.g., in order to provide structural support. Optionally, a clamping mechanism (not shown) is formed in the inner portion 706 and/or outer portion 710 in order to retain the device within the receptacle 702. In certain embodiments, the middle portion 708 is relatively thin (e.g., has a thickness similar to the thickness of the device), e.g., in order to facilitate air flow over and under the device for improved air circulation and thermal transport.

FIG. 7B illustrates a rotor assembly 720 similar to the rotor assembly 700, except that the outer portion 722 of the assembly 720 is formed as discrete sections rather than extending continuously around the perimeter. In some embodiments, the outer portion 722 includes a plurality of gaps 724 interspersed between the discrete sections such that the middle portion 726 extends to the edge of the rotor assembly 720 at the gaps 724. This design provides additional improvements to air circulation, in some embodiments. FIG. 7C illustrates a rotor assembly 740 similar to the rotor assembly 720, except that additional openings 742 are formed in the middle portion 744 of the assembly 740 to further improve air flow. Optionally, the openings 742 are angled similar to fan blades in order to facilitate convective air flow and thermal transport when the rotor assembly 740 is spinning, e.g., during convective thermal cycling.

In certain embodiments, heating and/or cooling is applied to the microfluidic devices received with the rotor assembly in accordance with a sequence or protocol, such as a dPCR thermal cycling procedure. In various embodiments, a thermal cycling procedure involves alternatingly heating and cooling one or more fluidic samples (e.g., contained within fluidic compartments of a microfluidic device) over a plurality of cycles in order to amplify a target analyte (e.g., a nucleic acid). The conditions for performing thermal cycling for analyte amplification are known to those of ordinary skill in the art. Optionally, the application of heating and/or cooling is controlled by one or more processors configured with suitable instructions for controlling the operation of the self-digitization system, as discussed further herein.

In order to improve the efficiency and uniformity of sample heating and/or cooling, certain embodiments herein include a housing enclosing one or more components of the self-digitization system, such as the rotor assembly, rotary actuator, heating device, and/or cooling device. Additionally, in some embodiments, the housing also protects the components of the system from damage and/or contamination, and also protects users from rapidly rotating parts and other potential safety hazards. In various embodiments, one or more portions of the housing (e.g., at least one housing wall) are provided with insulating structures in order to reduce undesirable thermal conduction to or from the system. Optionally, one or more insulating structures are coupled to components of the system that may be sensitive to temperature fluctuations, excessively high temperatures, and/or excessive low temperatures, such as one or more portions of the rotary actuator (e.g., a rotor shaft).

In some embodiments, the self-digitization system includes a ventilation assembly configured to control air flow around the heating device, cooling device, and/or rotor assembly, e.g., to produce more uniform heating and/or cooling of the microfluidic devices. Exemplary ventilation assembly components include one or more of fans, ducting, air inlets, air outlets, and the like.

Figure 8:
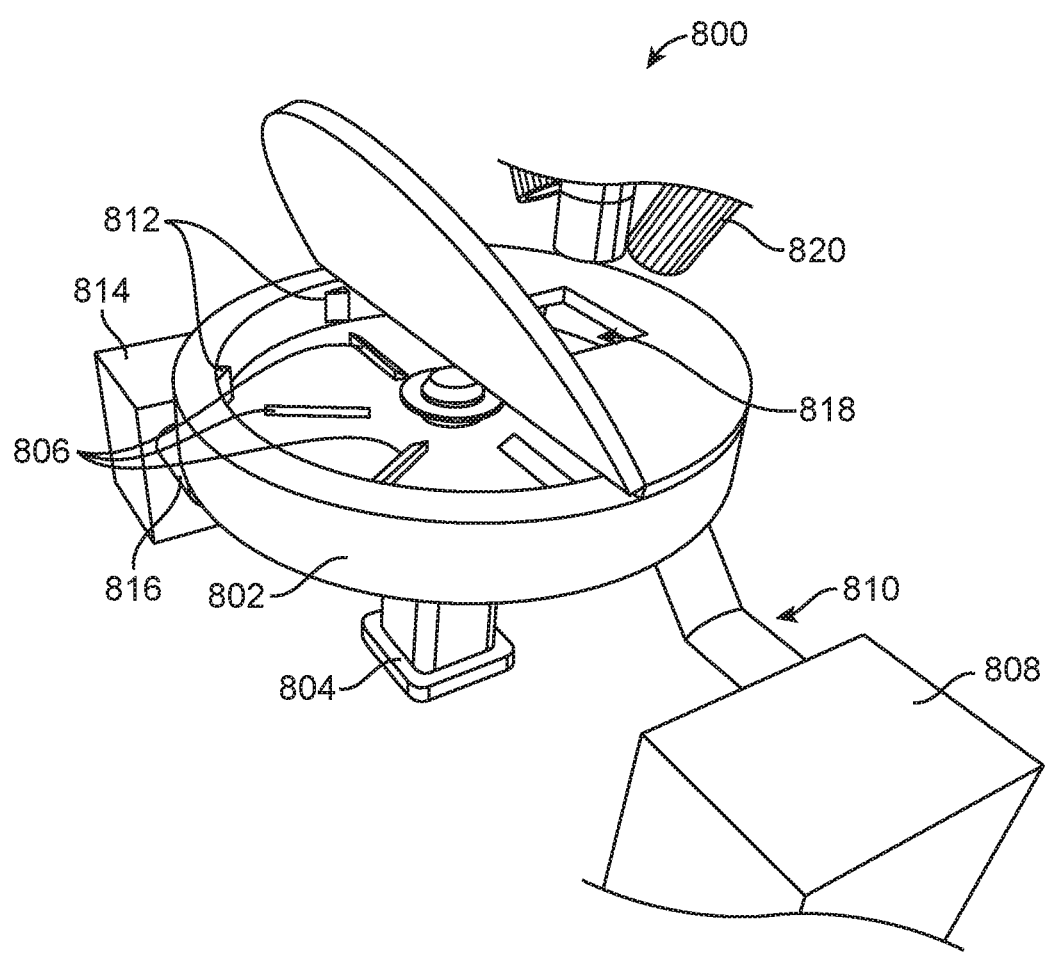
FIG. 8 illustrates a portion of a system for heating and/or cooling of microfluidic devices.

FIG. 8 illustrates a portion of a system 800 configured for heating and/or cooling of microfluidic devices, in accordance with embodiments. In some embodiments, the system 800 includes an insulated chamber 802 enclosing the rotor assembly. The rotary actuator (e.g., motor 804) for rotating the rotor assembly optionally extends at least partially outside of the chamber 802. In certain embodiments, the system 800 includes a ventilation assembly for facilitating air flow and thermal transport into and out of the chamber 802, such as one or more air intake vents 806 formed in the chamber 802, an air intake and heating unit 808 coupled to the chamber 802 (e.g., via air intake duct 810), one or more air exhaust vents 812 formed in the chamber 802, and/or an air exhaust unit 814 coupled to the chamber 802 (e.g., via air exhaust duct 816). In some embodiments, the system 800 includes a heating device inside the chamber, rather than external to the chamber or in combination therewith. Optionally, the chamber 802 includes one or more windows 818 that permit other functional components to access the microfluidic devices from outside the chamber 802, such as an imaging device 820 as discussed further herein.

In some embodiments, the self-digitization system includes a heating device composed of one or more devices which emit ultra violet radiation, emit visible radiation, emit infrared radiation, or emit a combination of two or more types of radiation. These radiation emitting heating devices will be referred to as lamps. Alternately or in combination, any combination of these lamps may be used. During heating, the lamps will be positioned to transfer heat to the microfluidic device. The lamps will irradiate the microfluidic device directly, irradiate a radiation absorbing material which then transfers heat to the microfluidic device, or a combination thereof. The lamps will be positioned below the rotor, above the rotor, alongside the rotor, or a combination thereof. The lamps will be aligned with the microfluidic device by moving the microfluidic devices to be aligned with the lamps, moving the lamps so that they are aligned with the microfluidic devices, or a combination thereof. In some embodiments, the configuration and/or number of lamps renders this alignment step unnecessary. In some embodiments, the lamps are attached to the rotor, attached inside the chamber but not directly to the rotor, or a combination thereof. In some embodiments, mirrors are used to direct radiation from the lamps on to the microfluidic device, on to a radiation absorbing material which then transfers heat to the microfluidic device, or a combination thereof.

Optionally, improved accuracy over the application of heating and/or cooling is achieved using feedback mechanisms, e.g., feedback based on temperature data received from one or more temperature sensors. In some embodiments, one or more temperature sensors are used to monitor the temperature of the microfluidic devices, rotor assembly, and/or interior air temperature of the housing. In certain embodiments, the temperature data is received by one or more processors configured with instructions to cause the system to adjust an amount of heating applied by the heating device and/or an amount of cooling applied by the cooling device in response to the temperature data.

Various embodiments of the systems, methods, and devices herein are suitable for obtaining measurements of the fluidic samples contained within the microfluidic devices. In some embodiments, measurement data is obtained after the fluidic samples have been discretized and/or processed (e.g., via heating, cooling, thermal cycling, etc.) to determine the presence and/or amount of a target analyte present in the fluidic samples. For instance, in certain embodiments, the systems herein are used to quantify an amount of a nucleic acid amplified via dPCR thermal cycling as discussed herein.

In some embodiments, the system includes an imaging device configured to obtain image data of the microfluidic devices received within the rotor assembly. In certain embodiments, the image data is bright-field image data, phase contrast image data, or fluorescence image data. In certain embodiments, the imaging modality is selected based on the properties of the target analyte in the fluidic sample, e.g., fluorescence imaging is used if the target analyte is fluorescent. Any imaging device with sufficient resolution for resolving the individual fluidic compartments of the device can be used with the systems, methods, and devices herein. For instance, in some embodiments, the imaging device is a microscope, such as a confocal microscope, spinning disk microscope, multi-photon microscope, planar illumination microscope, Bessel beam microscope, differential interference contrast microscope, phase contrast microscope, epifluorescent microscope, or a combination thereof. In some embodiments, a detector used in the systems, methods, and devices herein can be a device capable of capturing an image such as a charged coupled device (CCD) camera or a complementary metal-oxide-semiconductor (CMOS) camera, a device with a single element sensitive to light such as an avalanche photo diode (APD) or photomultiplier tube (PMT), a hybrid device such as a multielement APD or multielement PMT, or any combination thereof. As another example, in some embodiments, the imaging device is a camera, such as a CCD camera or a CMOS camera. For example, the optics can comprise a single lens, a multielement lens, an optical filter, a mirror, a beam splitter, or any combination thereof. Optionally, imaging of the microfluidic devices is controlled by one or more processors configured with suitable instructions for controlling the operation of the self-digitization system, as discussed further herein. In such embodiments, the imaging is configured to be controlled by a computer or other processing device via suitable software.

In certain embodiments, the imaging device is a digital single-lens reflex (DSLR) camera, e.g., with sufficient sensitivity and image resolution for performing fluorescence imaging. In some embodiments, a DSLR camera-based imaging setup is advantageous in terms of being relatively low cost while providing satisfactory image resolution. The configuration of the DSLR camera (e.g., ISO, F number, exposure time, focusing mode, etc.) can be varied as desired. In certain embodiments, the ISO, F number, and exposure time are fixed for a set of image data in order to permit comparison of signal intensities across different images. In some embodiments, the DSLR camera is used with a macro lens, e.g., having a lens mount matching the camera body.

In some embodiments, the imaging device is configured to obtain image data (e.g., fluorescence image data) of the microfluidic devices. In certain embodiments, the field of view of the imaging device is sized to capture a portion of a microfluidic device in a single image. For instance, in various embodiments, the imaging device comprises a field of view sized to capture at least 10%, at least 20%, at least 30%, at least 40%, at least 50%, at least 60%, at least 70%, at least 80%, at least 90%, or at least 100% of a surface area of the body of a single microfluidic device in a single image.

In other embodiments, the field of view of the imaging device is sized to capture the entirety of a single microfluidic device in a single image. In yet other embodiments, the field of view of the imaging device is sized to capture the entirety of a plurality of microfluidic devices in a single image. Optionally, the field of view is adjustable, e.g., according to user preference. In various embodiments, the imaging device comprises a field of view sized to capture at least 500, at least 1000, at least 1500, at least 2000, at least 2500, at least 3000, at least 3500, at least 4000, at least 4500, at least 5000, at least 10,000, at least 50,000, or at least 100,000 fluidic compartments of a single microfluidic device in a single image.

Subsequently, the image data is processed (e.g., with aid of one or more processors of the system) in order to measure a characteristic (e.g., fluorescence) from the fluidic compartments of the microfluidic devices. For instance, in some embodiments, the processing involves determining a signal intensity (e.g., fluorescence intensity) from each fluidic compartment of the imaged microfluidic device in order to determine the presence and/or concentration of a target analyte. A signal intensity above a threshold value indicates presence of the analyte while a signal intensity below the threshold value indicates the analyte is absent, in certain embodiments. This approach is suitable for use with various analytical techniques, such as dPCR. Alternatively or in combination, the processing involves determining a signal wavelength (e.g., fluorescence wavelength) from each fluidic compartment. This approach is advantageous for multiplexed analysis, for example.

In certain embodiments, the imaging devices include and/or are used in combination with one or more illumination sources, such as an illumination source configured to provide substantially uniform flooding illumination, e.g., over the portion of the device to be imaged. Various configurations of the illumination source and imaging device can be used. The optical axis of the imaging device and the principal rays of the illumination sources can form an angle between 0 and 10 degrees, between 10 and 20 degrees, between 20 and 30 degrees, between 30 and 45 degrees, between 45 and 60 degrees, between 60 and 75 degrees, between 75 and 90 degrees, between 90 and 105 degrees, between 105 and 120 degrees, between 120 and 135 degrees, between 135 and 150 degrees, between 150 and 160 degrees, between 160 and 170 degrees, or between 170 and 180 degrees. Alternately, or in combination, illumination sources at any combination of these angles are used. Angles greater than 90 degrees indicate that the illumination source(s) are on the opposite side of the microfluidic device from the imaging device. When the angle between the optical axis of the imaging device and the principal rays of the illumination source is between 0 and 10 degrees or between 170 and 180 degrees, the illumination is referred to as direct illumination. When the angle is between 10 and 170 degrees, the illumination is referred to as oblique. For instance, in some embodiments, direct illumination is used, e.g., in which the optical axis of the imaging device is substantially parallel to the principal rays of the illumination source(s). Alternatively or in combination, oblique illumination is used, e.g., in which the optical axis of the imaging device is not parallel to the principal rays of the illumination source(s). In some embodiments, the illumination source includes one or more light-emitting diodes (LEDs), such as a white light LED or colored LED, and the LEDs can be positioned relative to the imaging device in order to provide direct and/or oblique illumination, as desired. In some embodiments, the illumination source includes a ring illumination source positioned around the imaging device and configured to provide direct and/or oblique illumination, as desired. In some embodiments, the illumination can be arranged in an epi-fluorescence configuration as the term is known in the art, e.g., to provide direct illumination.

Optionally, in embodiments where the fluidic sample includes one or more fluorophores, the illumination source is configured to produce light energy at an excitation wavelength of the one or more fluorophores, and the imaging device is configured to measure light energy at an emission wavelength of the one or more fluorophores. The embodiments herein are suitable for accommodating a wide variety of excitation wavelengths (e.g., within a range from approximately 350 nm to approximately 850 nm) and emission wavelengths (e.g., within a range from approximately 400 nm to approximately 900 nm). In certain embodiments, suitable excitation and/or emission filters are used to filter light transmitted to and/or received from the fluidic sample, respectively. Optionally, excitation filters are not used if the illumination source is configured to produce the desired wavelength of light (e.g., a color LED).

Figure 9A:
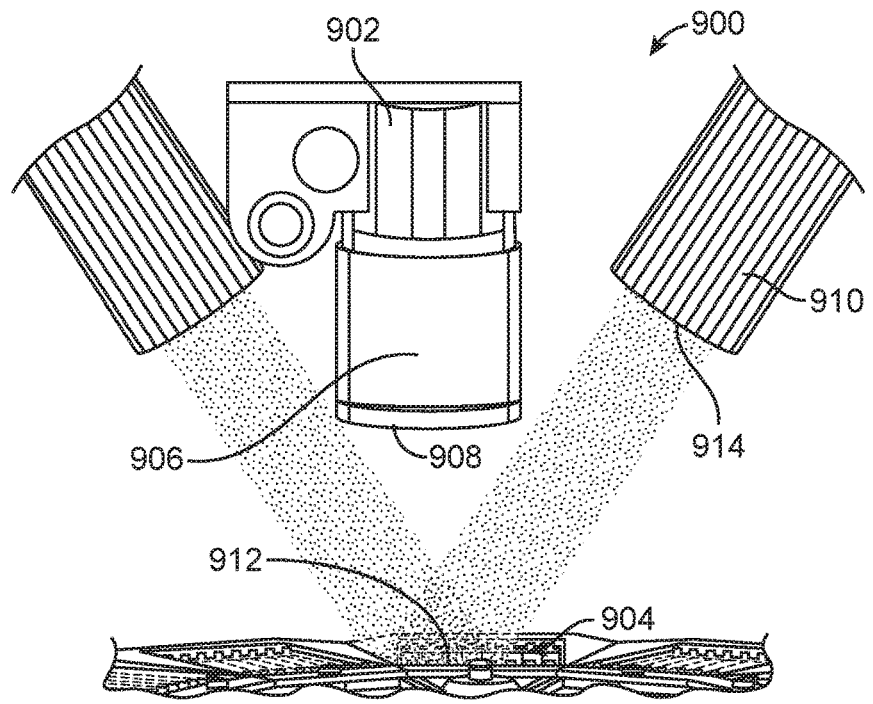
FIG. 9A illustrates an oblique illumination configuration for imaging a microfluidic device.

FIG. 9A illustrates an oblique illumination configuration 900 for imaging a microfluidic device 902 using a DSLR camera 904, in accordance with embodiments. It shall be appreciated that in alternative embodiments, the configuration 900 can be adapted for use with other types of imaging devices. In some embodiments, the camera 904 includes a macro lens 906 and an emission filter 908 coupled to the lens 906 for receiving light having a specified emission wavelength. One or more illumination sources 910 (e.g., LED illumination sources) are positioned laterally from the camera 904 and oriented towards the device 902 so as to form an illuminated region 912 over at least a portion of the device 902. Optionally, the illumination sources 910 include an excitation filter 914 for providing light having a specified excitation wavelength. In alternative embodiments, the excitation filter 914 is omitted, e.g., when using a LED configured to emit light with the excitation wavelength. In certain embodiments, the illumination sources 910 are oriented at an angle relative to the optical axis of the camera 904 so as to provide oblique illumination of the device 902. In some embodiments, the illuminated region 912 covers the entirety of the device 902, while in other embodiments, the illuminated region 912 covers only a portion of the device 902. In the latter case, the camera 904 and/or illumination sources 910 are coupled to a movement stage or other actuation mechanism so as to sequentially illuminate and image different portions of the device 902. In some embodiments, the configuration 900 has identifiers that facilitate alignment of device 904 or a portion thereof, e.g., a single well or multiple specific wells, for imaging with DSLR camera 902 or an alternative imaging device. Optionally, such identifiers are used to define illuminated region 912.

Figure 9B:
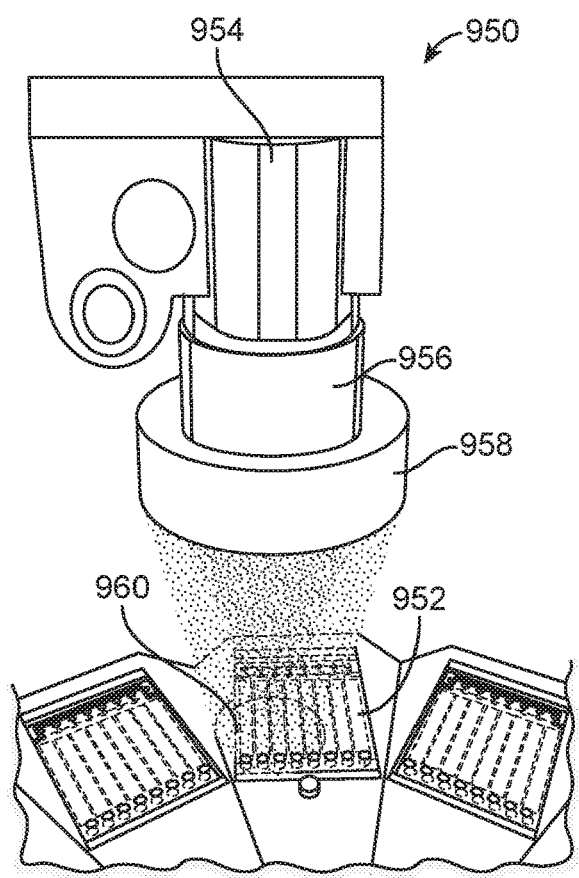
FIG. 9B illustrates a direct illumination configuration for imaging a microfluidic device.

FIG. 9B illustrates a direct illumination configuration 950 for imaging a microfluidic device 952 using a DSLR camera 954, in accordance with embodiments. It shall be appreciated that in alternative embodiments, the configuration 950 can be adapted for use with other types of imaging devices. In some embodiments, the camera 954 includes a macro lens 956. One or more illumination sources 958 are coupled to the camera 954 (e.g., coupled to the macro lens 956) and oriented with a small angle to the optical axis of the camera 954 so as to form an illuminated region 960 over at least a portion of the device 952 and thereby provide direct illumination of the device 952. In certain embodiments, the illumination source 958 is a ring illumination source (e.g., a LED ring light) positioned around at least a portion of the camera 954 (e.g., around the macro lens 956). Optionally, additional filters and/or other optical components are coupled to the camera 954, macro lens 956, and/or illumination source(s) 958, e.g., to provide light having a specified excitation wavelength and/or receive light having a specified emission wavelength. In some embodiments, the illuminated region 960 covers the entirety of the device 952, while in other embodiments, the illuminated region 960 covers only a portion of the device 952. In the latter case, the camera 954 and/or illumination source(s) 958 are coupled to a movement stage or other actuation mechanism so as to sequentially illuminate and image different portions of the device 952. In some embodiments, the configuration 950 has identifiers that facilitate alignment of device 952 or a portion thereof, e.g., a single well or multiple specific wells, for imaging with DSLR camera 954 or an alternative imaging device. Optionally, such identifiers are used to define illuminated region 960. In some embodiments, the instrument can identify, using the identifiers, the position and orientation of the microfluidic chip relative to the imaging device thereby identifying which portions of the image to analyze.

The various components (e.g., rotary actuator, heating device, cooling device, temperature sensor, ventilation assembly, imaging device, illumination source, etc.) of the self-digitization systems described herein can be configured in multiple ways. In some embodiments, one or more of the components herein are positioned above the rotor assembly and received microfluidic devices. In some embodiments, one or more of the components herein are positioned below the rotor assembly and received microfluidic devices. In some embodiments, one or more of the components herein are positioned on the rotor assembly, such as coupled to the rotor assembly.

In some embodiments, one or more of the components herein (e.g., rotary actuator, heating device, cooling device, temperature sensor, ventilation assembly, imaging device, illumination source, etc.) are movable, such that the position of the component(s) relative to the rotor assembly is adjustable. For instance, in certain embodiments, a component is positioned near the rotor assembly when the component is operating, and is positioned away from the rotor assembly when the component is not operating. Optionally, the component is positioned near the rotor assembly when the rotor assembly is not rotating, and is positioned away from the rotor assembly when the rotor assembly is rotating.

In some embodiments, an actuation mechanism (e.g., motor) is provided in order to adjust the positions of one or more movable components relative to the rotor assembly and/or microfluidic devices. Optionally, operation of the actuation mechanism is controlled by one or more processors configured with suitable instructions for controlling the operation of the self-digitization system, as discussed further herein. In certain embodiments, the actuation mechanism is also configured to operably couple one or more components (e.g., rotary actuator, heating device, cooling device, temperature sensor, ventilation assembly, imaging device, illumination source, a power source, etc.) to the rotor assembly. A component can be operably coupled to the rotor assembly with or without direct contact with the rotor assembly. For example, in some embodiments, a heating device is thermally coupled to the rotor assembly in order to apply heat to the microfluidic devices via direct contact between the heating device and the rotor assembly and/or microfluidic devices. In alternative embodiments, the heating devices are thermally coupled to the rotor assembly without direct contact between the heating device and the rotor assembly and/or microfluidic devices (e.g., there is an air gap between the heating device and the rotor assembly and/or microfluidic devices).

In some embodiments, one or more heating devices are coupled to an actuation mechanism that translates and/or rotates the heating device(s) in order to thermally couple the heating device(s) with one or more microfluidic devices (or a portion thereof) to perform heating. For instance, in certain embodiments, the heating device(s) are positioned below the rotor assembly and the actuation mechanism raises the heating device(s) in order to heat the microfluidic devices. Alternatively or in combination, the rotor assembly is moved (e.g., translated and/or rotated) in order to thermally couple one or more microfluidic devices with the heating device(s).

Similarly, in some embodiments, one or more cooling devices are coupled to an actuation mechanism that translates and/or rotates the cooling device(s) in order to thermally couple the cooling device(s) with one or more microfluidic devices (or a portion thereof) to perform cooling. For instance, in certain embodiments, the cooling device(s) are positioned below the rotor assembly and the actuation mechanism raises the cooling device(s) in order to cool the microfluidic devices. Alternatively or in combination, the rotor assembly is moved (e.g., translated and/or rotated) in order to thermally couple one or more microfluidic devices with the cooling device(s).

As another example, in some embodiments, the imaging device is coupled to an actuation mechanism that translates and/or rotates the imaging device in order to align the imaging device (e.g., the field of view of the imaging device) with one or more microfluidic devices (or a portion thereof) to perform imaging. In embodiments where the field of view of the imaging device covers only a portion of the microfluidic device, the imaging device is moved to a plurality of different positions and/or orientations in order to allow for imaging of the entirety of the microfluidic device. Alternatively or in combination, the rotor assembly is moved (e.g., translated and/or rotated) in order to align one or more microfluidic devices with the imaging device.

Figure 10:
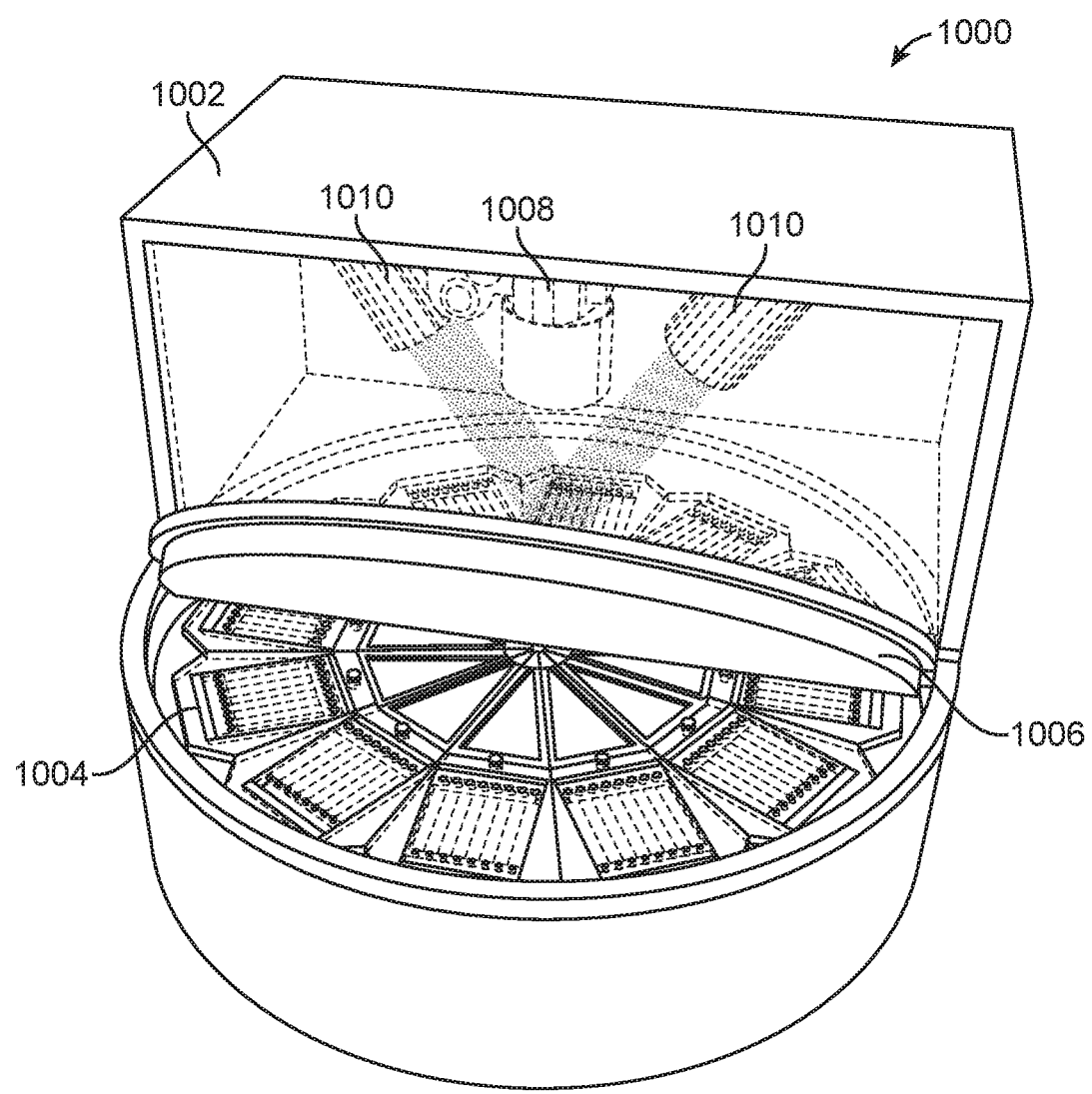
FIG. 10 illustrates a multifunctional system for discretization, heating, and imaging.

FIG. 10 illustrates an exemplary multifunctional system 1000 for sample discretization, heating, and imaging, in accordance with embodiments. The system 1000 can be used in combination with any embodiment of the methods and devices herein. The system 1000 includes a housing 1002 that partially or wholly encloses a rotor assembly 1004 for receiving a plurality of microfluidic devices. In some embodiments, the housing 1002 includes a lid 1006 allowing access to the rotor assembly 1004 (e.g., for loading and unloading microfluidic devices). The rotor assembly 1004 is coupled to a rotary actuator (not shown) for rotating the rotor assembly 1004, e.g., in order to drive fluid into the fluidic compartments of the received microfluidic devices to discretize a sample. A plurality of heating devices (not shown) are positioned below the rotor assembly 1004 for heating the microfluidic devices, e.g., in accordance with a thermal cycling procedure. In some embodiments, the number of heating devices corresponds to the number of receptacles in the rotor assembly 1004, such that each heating device is used to apply heat to a single respective microfluidic device. The system 1000 also includes an imaging device 1008 for imaging the microfluidic devices in the rotor assembly 1004 and one or more illumination sources 1010 for illuminating the microfluidic devices during imaging. In some embodiments, the imaging device 1008 and illumination sources 1010 are positioned above the rotor assembly 1004.

Figure 11C:
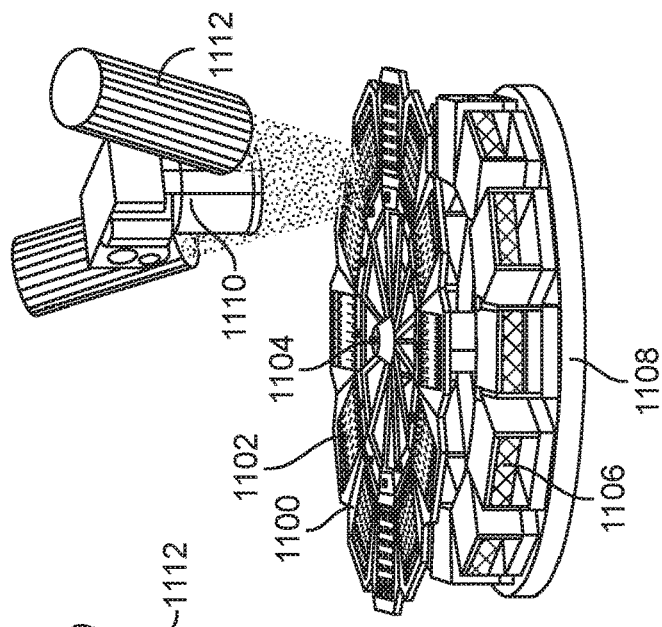
FIGS. 11A through 11C illustrate discretizing, heating, and imaging a plurality of fluidic samples using a multifunctional system, respectively.
Figure 11B:
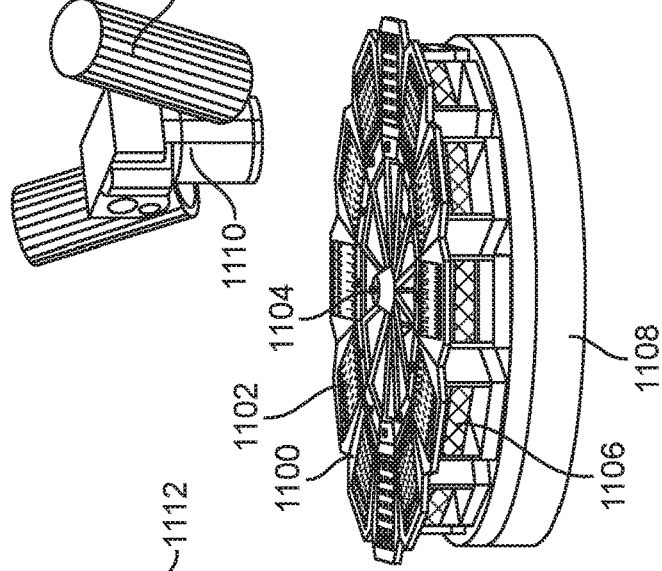
Figure 11A:
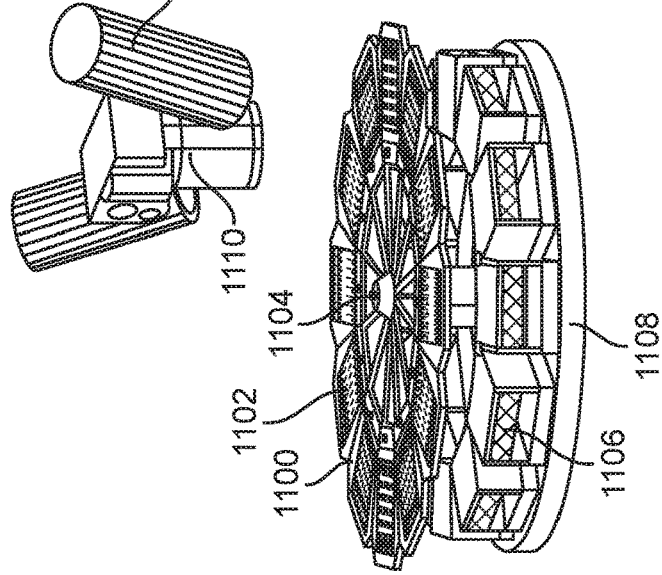

FIGS. 11A through 11C illustrate discretizing, heating, and imaging a plurality of fluidic samples using a multifunctional system, in accordance with embodiments. The steps of the method can be performed using any embodiment of the systems and devices herein. In some embodiments, the method is performed using a multifunctional self-digitization system including a rotor assembly 1100 configured to receive a plurality of microfluidic devices 1102, a rotary actuator 1104 (e.g., a stepper motor, servo motor, brushless direct current motor, etc.) for rotating the rotor assembly 1100, a plurality of heating devices 1106 (e.g., Peltier units) coupled to an actuation mechanism 1108 (e.g., a stage or other positional control system) and positioned below the rotor assembly 1100, and an imaging system positioned above the rotor assembly 1100 including an imaging device 1110 and at least one illumination source 1112. Optionally, the system includes an encoder or other position information system for monitoring and/or controlling the position of the rotor assembly 1100 relative to the heating devices 1106 and/or the imaging system.

FIG. 11A illustrates sample discretization using the multifunctional system. As discussed above and herein, sample discretization is performed by rotating the microfluidic devices 1102 in the rotor assembly 1100 at a rotational speed sufficient to drive a fluidic sample into at least a subset of the fluidic compartments in the received microfluidic devices. The rotary actuator 1102 is used to rotate the rotor assembly 1100 at a controlled speed. In some embodiments, the plurality of heating devices 1106 and actuation mechanism 1108 are in a lowered position away from the rotor assembly 1100 during the discretization step in order to allow for rotation of the rotor assembly 1100.

FIG. 11B illustrates sample heating using the multifunctional system. The sample heating step is optionally performed after the sample discretization step. In some embodiments, the actuation mechanism 1108 is used to raise the heating devices 1106 towards the rotor assembly 1100 in order to thermally couple the heating devices 1106 to the microfluidic devices 1102. The thermal coupling may or may not involve direct contact between the heating devices 1106 and the microfluidic devices 1102. In some embodiments, the rotor assembly 1100 is stationary during the heating step. In alternative embodiments, such as when convective heating is used, the rotor assembly 1100 is rotating during the heating step, e.g., to improve air circulation for uniform heating.

FIG. 11C illustrates sample imaging using the multifunctional system. The sample imaging step is optionally performed after the sample heating step. In some embodiments, the rotor assembly 1100 is rotated by the actuator 1102 through a plurality of rotational positions in order to sequentially align each microfluidic device 1102 with the imaging device 1110 and illumination source 1112 for imaging. In certain embodiments, the plurality of heating devices 1106 and actuation mechanism 1108 are in a lowered position away from the rotor assembly 1100 during the imaging step in order to accommodate rotation of the rotor assembly 1100.

As discussed above and herein, the operation of the self-digitization systems herein can be controlled by one or more processors configured with suitable instructions in order to perform the various methods herein. In some embodiments, for example, the systems described herein include a computer comprising one or more processors and a memory device with executable instructions stored thereon. In some embodiments, the computer is used to perform the methods described herein. In various embodiments, a computer can be used to implement any of the systems or methods illustrated and described above. In some embodiments, a computer includes a processor that communicates with a number of peripheral subsystems via a bus subsystem. These peripheral subsystems can include a storage subsystem, comprising a memory subsystem and a file storage subsystem, user interface input devices, user interface output devices, and a network interface subsystem.

In some embodiments, a bus subsystem provides a mechanism for enabling the various components and subsystems of the computer to communicate with each other as intended. The bus subsystem can include a single bus or multiple busses.

In some embodiments, a network interface subsystem provides an interface to other computers and networks. The network interface subsystem can serve as an interface for receiving data from and transmitting data to other systems from a computer. For example, a network interface subsystem can enable a computer to connect to the Internet and facilitate communications using the Internet.

In some embodiments, the computer includes user interface input devices such as a keyboard, pointing devices such as a mouse, trackball, touchpad, or graphics tablet, a scanner, a barcode scanner, a touch screen incorporated into the display, audio input devices such as voice recognition systems, microphones, and other types of input devices. In general, use of the term "input device" is intended to include all possible types of devices and mechanisms for inputting information to a computer.

In some embodiments, the computer includes user interface output devices such as a display subsystem, a printer, a fax machine, or non-visual displays such as audio output devices, etc. The display subsystem can be a cathode ray tube (CRT), a flat-panel device such as a liquid crystal display (LCD), or a projection device. Output devices are not limited to any particular device, and can include, for example, interactive displays, touchpads, touchscreens, as well as mobile devices such as smartphones and tablets. In general, use of the term "output device" is intended to include all possible types of devices and mechanisms for outputting information from a computer.

In some embodiments, the computer includes a storage subsystem that provides a computer-readable storage medium for storing the basic programming and data constructs. In some embodiments, the storage subsystem stores software (programs, code modules, instructions) that when executed by a processor provides the functionality of the methods and systems described herein. These software modules or instructions can be executed by one or more processors. A storage subsystem can also provide a repository for storing data used in accordance with the present disclosure. The storage subsystem can include a memory subsystem and a file/disk storage subsystem.

In some embodiments, the computer includes a memory subsystem that can include a number of memories including a main random access memory (RAM) for storage of instructions and data during program execution and a read only memory (ROM) in which fixed instructions are stored. A file storage subsystem provides a non-transitory persistent (non-volatile) storage for program and data files, and can include a hard disk drive, a floppy disk drive along with associated removable media, a Compact Disk Read Only Memory (CD-ROM) drive, an optical drive, removable media cartridges, and other like storage media.

The computer can be of various types including a personal computer, a portable computer, a workstation, a network computer, a mainframe, a kiosk, a server or any other data processing system. Due to the ever-changing nature of computers and networks, the description of computer contained herein is intended only as a specific example for purposes of illustrating the embodiments of the computer. Many other configurations having more or fewer components than the system described herein are possible.

Methods for Self-Digitization, Processing, and Analysis of Fluidic Samples

Various methods for performing sample discretization, processing, and analysis are suitable for use in combination with the embodiments herein. In some embodiments, a method for discretizing and analyzing a fluidic sample comprises: providing a microfluidic device as in any of the embodiments herein; applying a fluidic sample comprising a plurality of discrete analytes to the fluid inlet ports of the microfluidic device; and rotating the microfluidic device such that the plurality of discrete analytes are driven into a subset (e.g., less than all) of the plurality of fluidic compartments of the microfluidic device, thereby discretizing the fluidic sample into a plurality of fluidic packets defined by the compartments. Optionally, the microfluidic device is configured for use with a multi-channel pipette and the fluidic sample is applied to the fluid inlet ports using a multi-channel pipette.

In some embodiments, the discretization of the fluidic sample involves sequentially introducing a plurality of different fluids into the microfluidic device. For example, in certain embodiments, the method comprises applying a first fluid to the microfluidic device (e.g., using a multi-channel pipette), and rotating the microfluidic device to drive the first fluid into the flow channels and/or fluidic compartments of the device. In various embodiments, the first fluid includes an oil that is introduced into device, e.g., to displace any air bubbles. In certain embodiments, the method comprises applying a second fluid (e.g., an aqueous solution) comprising the fluidic sample into the microfluidic device via the fluid inlet ports, and rotating the microfluidic device to drive the second fluid into the fluidic compartments and displace the first fluid (e.g., the oil) from the fluidic compartments. After the second fluid is loaded, a third fluid (e.g., an oil that may or may not be the same oil as the first fluid), is applied to the microfluidic device, and the device is rotated to displace the second fluid from the channels, but not the fluidic compartments. As a result, the fluidic sample is compartmentalized into discrete volumes determined by the fluidic compartment dimensions.

As discussed above and herein, rotation of the microfluidic device can be performed in various ways. In various embodiments, rotating the microfluidic device comprises: providing a rotor assembly comprising a central axis and a plurality of receptacles arranged radially around the central axis; positioning the microfluidic device in one of the plurality of receptacles such that the proximal body portion of the microfluidic device is positioned near the central axis and the distal body portion of the microfluidic device is positioned away from the central axis; and rotating the rotor assembly around the central axis, thereby rotating the microfluidic device.

In certain embodiments, the methods of the present disclosure are used to discretize a fluidic sample including a plurality of nucleic acid molecules, e.g., for PCR applications such as dPCR. In some embodiments, a fluid sample including a plurality of nucleic acid molecules is applied to the fluid inlet ports of a microfluidic device. By rotating the microfluidic device as described herein, the nucleic acid molecules are discretized within the fluidic compartments arranged in the devices, such that e.g., at least one nucleic acid molecule is present in at least some of the fluidic compartments. In some embodiments, the nucleic acid molecules are discretized such that no more than one nucleic acid molecule is present in at least some or all of the fluidic compartments. Alternatively, in some embodiments, the nucleic acid molecules are discretized such that more than one nucleic acid molecule is present in at least some of the fluidic compartments. In some embodiments, the nucleic acid molecules are discretized such that at least one of the fluidic compartments does not include any nucleic acid molecules. The number of nucleic acid molecules in each fluidic compartment depends in some embodiments on the concentration of the nucleic acid molecules in the loaded fluidic sample and/or the size of the fluidic compartments. Optionally, reagents for performing PCR on the nucleic acid molecules are also present in the sample that is loaded on the device. In some embodiments, after loading and discretization of the nucleic acid molecules, PCR is conducted in situ in the microfluidic device, as discussed above and herein.

In some embodiments, the present disclosure provides methods for processing fluidic samples in a microfluidic device, subsequent to sample discretization. For instance, in certain embodiments, a method comprises applying heat to a microfluidic device in order to amplify a plurality of discrete analytes of a fluidic sample in the microfluidic device. As another example, in certain embodiments, a method comprises cooling the microfluidic device in order to reduce the temperature of the fluidic sample in the microfluidic device. In various embodiments, one or more heating and/or cooling cycles are performed in accordance with a dPCR thermal cycling protocols. For example, in certain embodiments, the fluidic sample in the microfluidic device comprises a plurality of nucleic acids and one or more dPCR reagents, and the heating and/or cooling is applied according to a dPCR thermal cycling procedure in order to amplify the plurality of nucleic acids using the one or more dPCR reagents.

In some embodiments, the present disclosure provides methods for analyzing fluidic samples in a microfluidic device, subsequent to sample discretization and/or processing. For instance, in certain embodiments, a method comprises obtaining image data of the microfluidic device using an imaging device. In various embodiments, image data is obtained by applying light energy to the plurality of discrete analytes within the plurality of fluidic compartments of the microfluidic device, and measuring a fluorescence signal from the plurality of discrete analytes within the plurality of fluidic compartments. The imaging is optionally performed while the microfluidic devices are positioned in the rotor assembly. For instance, in certain embodiments, the microfluidic device is positioned in a receptacle of the rotor assembly, and image data is obtained by rotating the rotor assembly in order to align the microfluidic device with the imaging device. Alternatively or in combination, the image data is obtained by translating and/or rotating the imaging device in order to align the microfluidic device with the imaging device.

In some embodiments, the methods of the present disclosure comprise providing a device and/or system in accordance with any of the embodiments herein.

The specific dimensions of any of the apparatuses, devices, systems, and components thereof, of the present disclosure can be readily varied depending upon the intended application, as will be apparent to those of skill in the art in view of the disclosure herein. Moreover, it is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present disclosure.

As used herein A and/or B encompasses one or more of A or B, and combinations thereof such as A and B.

All features discussed in connection with any embodiment or embodiment herein can be readily adapted for use in other embodiments and embodiments herein. The use of different terms or reference numerals for similar features in different embodiments does not necessarily imply differences other than those expressly set forth. Accordingly, the present disclosure is intended to be described solely by reference to the appended claims, and not limited to the embodiments disclosed herein.

Unless otherwise specified, the presently described methods and processes can be performed in any order. For example, a method describing steps (a), (b), and (c) can be performed with step (a) first, followed by step (b), and then step (c). Or, the method can be performed in a different order such as, for example, with step (b) first followed by step (c) and then step (a). Furthermore, those steps can be performed simultaneously or separately unless otherwise specified with particularity.

The particulars shown herein are by way of example and for purposes of illustrative discussion of the preferred embodiments of the present disclosure only and are presented in the cause of providing what is believed to be the most useful and readily understood description of the principles and conceptual embodiments of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

While preferred embodiments of the present disclosure have been shown and described herein, it is to be understood that the disclosure is not limited to the particular embodiments of the disclosure described, as variations of the particular embodiments can be made and still fall within the scope of the appended claims. It is also to be understood that the terminology employed is for the purpose of describing particular embodiments of the disclosure, and is not intended to be limiting. Instead, the scope of the present disclosure is established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the disclosure provided herein.

All features discussed in connection with an embodiment or embodiment herein can be readily adapted for use in other embodiments and embodiments herein. The use of different terms or reference numerals for similar features in different embodiments does not necessarily imply differences other than those expressly set forth. Accordingly, the present disclosure is intended to be described solely by reference to the appended claims, and not limited to the embodiments disclosed herein.

EXAMPLES

The following examples are included to further describe some aspects of the present disclosure, and should not be used to limit the scope of the invention.

Example 1

Imaging of a Microfluidic Device

This example describes an imaging procedure for obtaining image data of a microfluidic device using a DSLR camera.

Figure 12B:
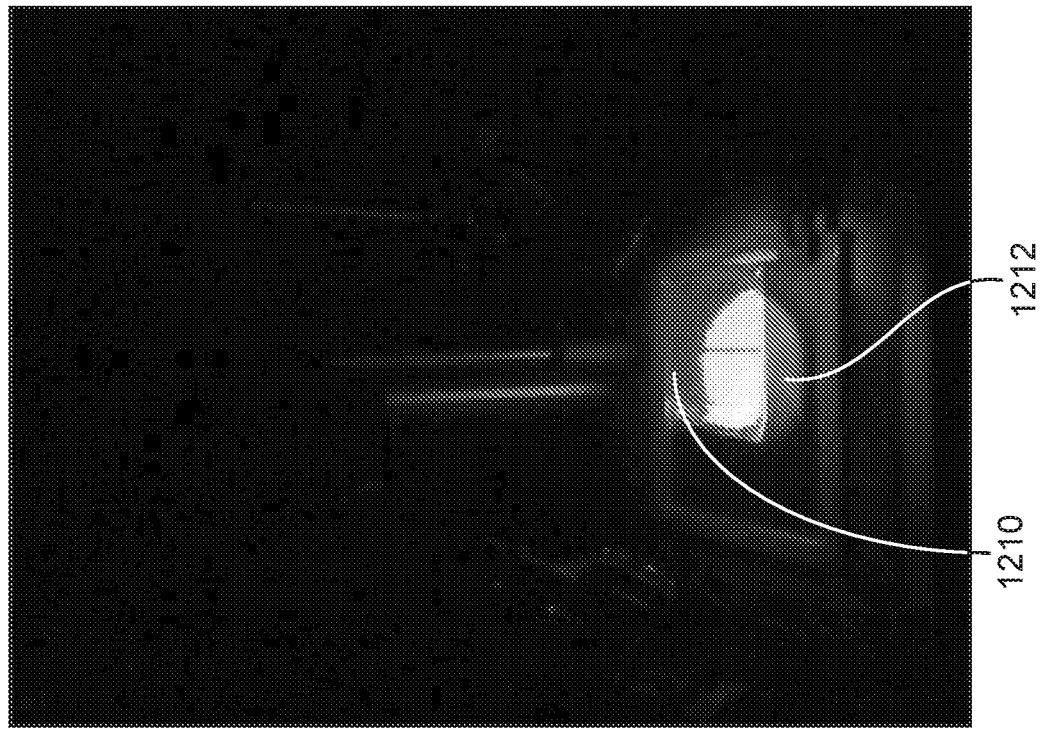
FIGS. 12A and 12B illustrate a configuration for imaging a microfluidic device.
Figure 12A:
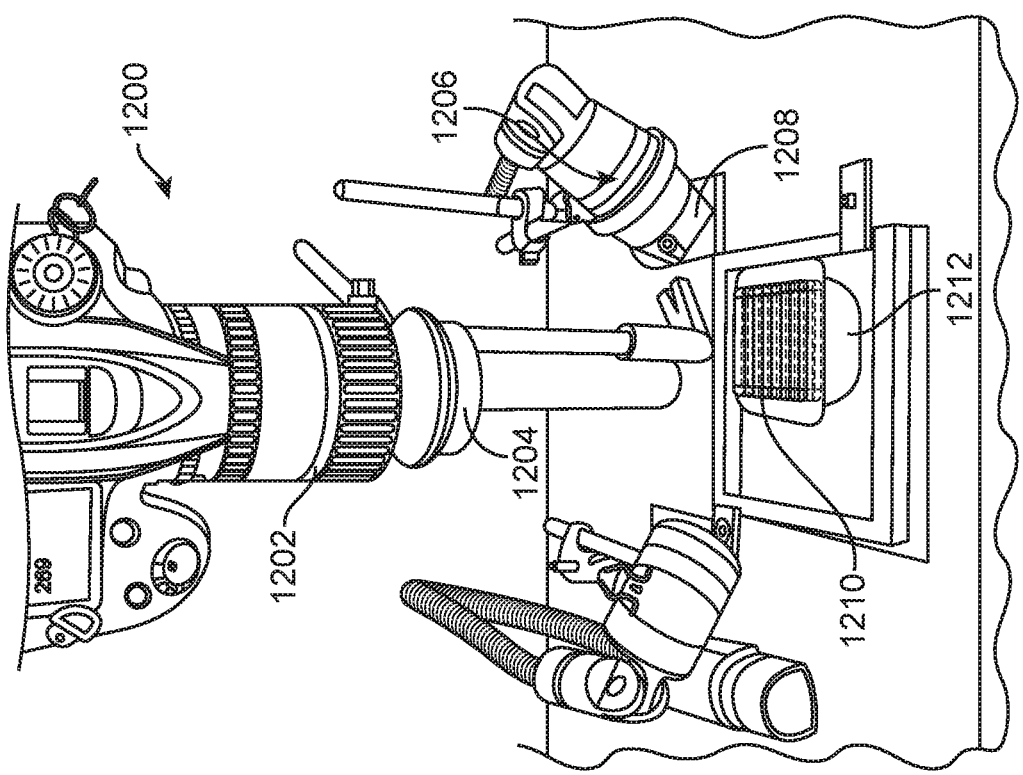

FIGS. 12A and 12B illustrate a configuration for imaging a microfluidic device. A DSLR camera 1200 with a macro lens 1202 is used. An emission filter 1204 is coupled to the front of the macro lens 1202. A pair of LED illumination sources 1206 with an excitation filter 1208 are used to provide oblique illumination of a microfluidic device 1210, thus producing an illuminated region 1212 on the device 1210.

The DSLR camera is a Nikon D7100 (24.1 MP, 6000 by 4000 pixels). The camera configuration is manual mode, back button focus enabled, ISO 800, aperture F 4.0, and 8 second exposure time for fluorescence images. The camera is controlled from a computer using a Labview-based software program. A Tokina 100 mm f/2.8 macro lens is used.

The illumination (excitation) source is a white light LED with an unfiltered output of approximately 200 Lumens. The excitation filter has a center wavelength of 475 nm with a bandwidth of 35 nm. The emission filter has a center wavelength of 520 nm with a bandwidth of 36 nm.

Images of the microfluidic device are obtained according the following procedure. First, the camera is turned on and connected to the computer in manual mode with back button focus enabled. Enabling back button focus prior to image acquisition ensures that the camera does not attempt to autofocus before the fluorescent image is acquired. This is significant as the fluorescence image is typically too dim for the camera's autofocus mechanism to focus correctly.

The microfluidic device is illuminated with a white light LED without the excitation filter. The software program controls the camera to focus on the device using autofocusing. Alternatively, the camera may be manually focused to the correct location and locked in the desired focal position. If desired, a white light image of the device is obtained. The white light LED is then turned off, and a different white light LED with the excitation filter is turned on. The exposure time is set to 8 seconds and a fluorescence image is acquired. The resolution of the camera is sufficient to image approximately one-fourth of the device at a time while maintaining adequate resolution to resolve individual compartments in the device. By moving the device and/or camera, four fluorescence images of the device are obtained and then analyzed.

Figure 13B:
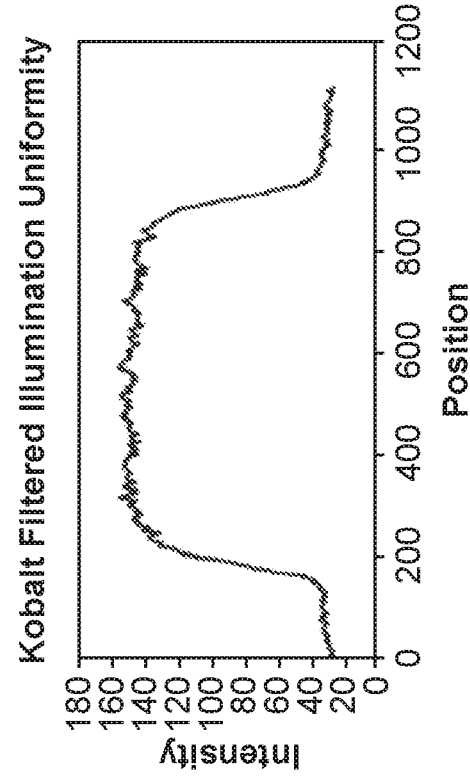
FIGS. 13A through 13D illustrate exemplary imaging results obtained with a camera.
Figure 13D:
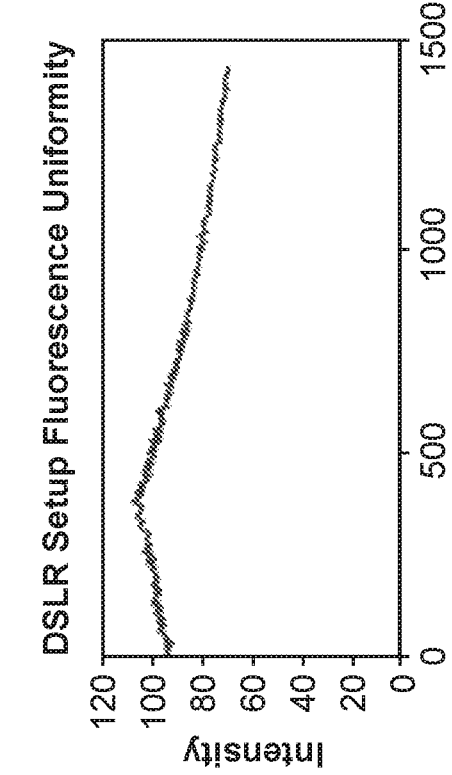
Figure 13A:
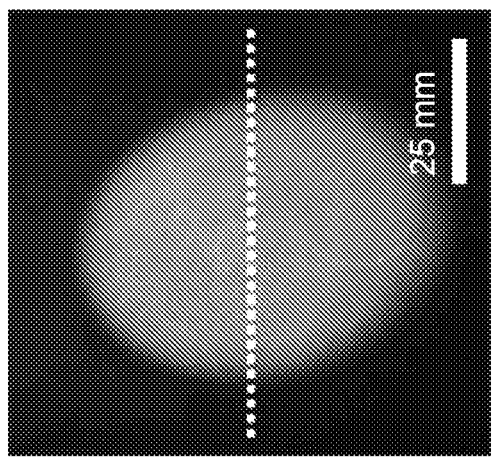
Figure 13C:
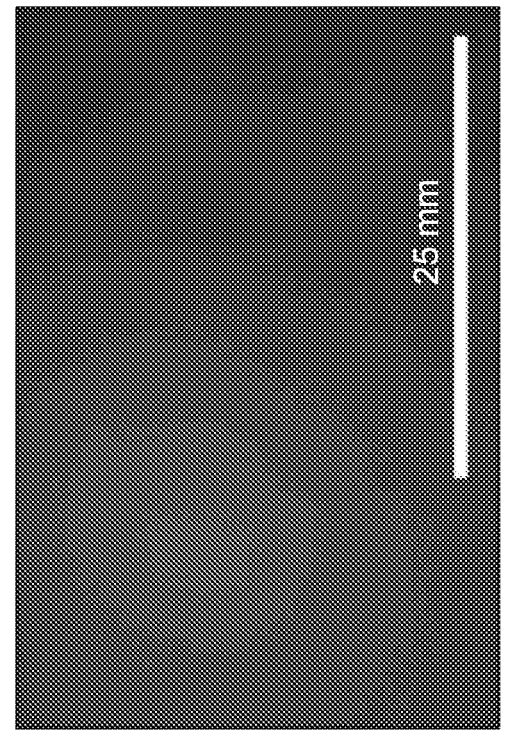

FIGS. 13A through 13D illustrate exemplary imaging results obtained with a DSLR camera. FIG. 13A is an image of the illuminated region. FIG. 13B is a graph illustrating the uniformity of the illumination over the illuminated region. FIG. 13C illustrates a fluorescence image obtained by the camera. FIG. 13D is a graph illustrating uniformity of the fluorescence captured by the camera.

Example 2

Loading of Linear Centrifuge Device

Figure 14:
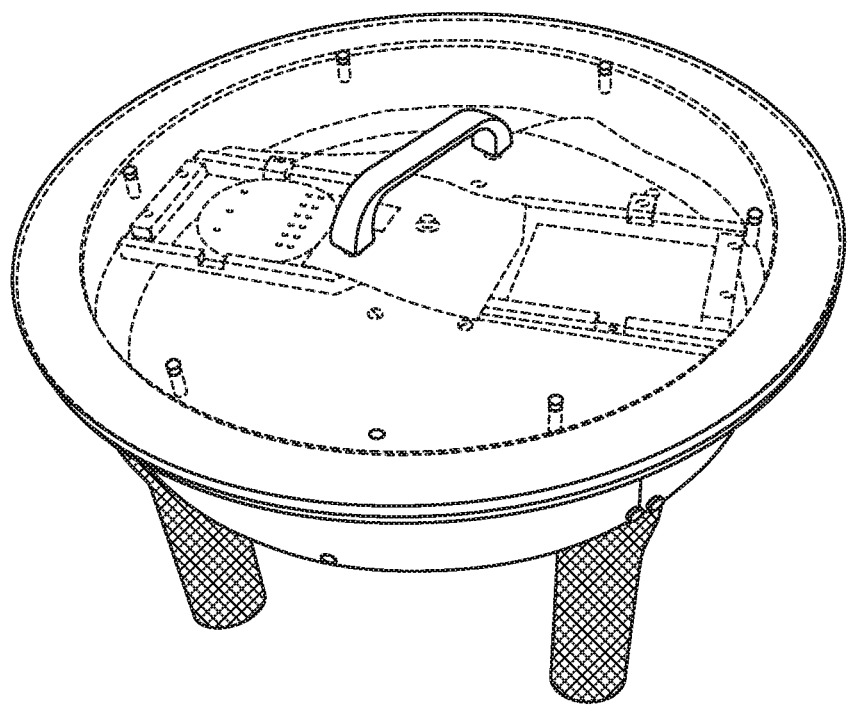
FIG. 14 provides an image of the loading instrument according to certain aspects of the disclosure.

This example describes loading of a linear centrifuge device. The loading instrument included a stepper motor as the rotary actuator, capable of 1600 microsteps/rotation and >1200 rotations per minute. Attached to the rotary actuator was the rotor assembly containing two receptacles for securing the microfluidic devices. The rotary assembly had a housing that also anchored the rotary actuator to enable safe rotation of the assembly and devices. The actuator was controlled through a computer on software provided by the manufacturer and/or distributor of the rotary actuator. FIG. 14 provides an image of the loading instrument described in some embodiments of this example.

In this embodiment each device could contain up to 8 arrays, with each array comprised of 2560 fluidic compartments, and each compartment comprising a volume of approximately 23 nL (see FIG. 4B). The devices (FIGS. 3A and 3B) consisted of a 3"×4" piece of glass that was spin-coated with PDMS. Bonded to this was another piece of PDMS containing the device features. This piece of PDMS consisted of three regions. The central region is thin (between 300-1000 μm thick) and spanned the entire area encompassing the fluidic compartments. The proximal region was thick (3-10 mm thick) and contained the inlets, inlet reservoirs, outlets and part of the channels that were in fluidic communication with the fluidic compartments. The distal region was also thick (2-10 mm thick) and contained outlet reservoirs and portions of the channels that allowed for fluidic communication with the fluidic compartments in the central region and the outlets in the proximal region. Over the central region a vapor barrier was bonded. In some embodiments this was glass, in other embodiments it was PCTFE, in other embodiments it was some other vapor barrier material. In some embodiments the vapor barrier was plasma sealed to the PDMS. In other embodiments an adhesive layer was used.

In one embodiment the typical oil used to preload the device was 0.02% Abil WE 09, 33% Tegosoft DEC and 67% light mineral oil. The device was degassed in a vacuum desiccator then the oil was loaded into the inlet reservoir and the device centrifuged in the rotor assembly at ~900-1200 RPM for 2-10 minutes. In some embodiments it was necessary to load additional oil into the inlet reservoir and additional rounds of centrifuging were performed. In some embodiments the partly loaded device was placed in the vacuum desiccator under low vacuum pressure to continue to evacuate air bubbles. Once all air bubbles were removed from the wells the device could be loaded with sample.

Figure 15:
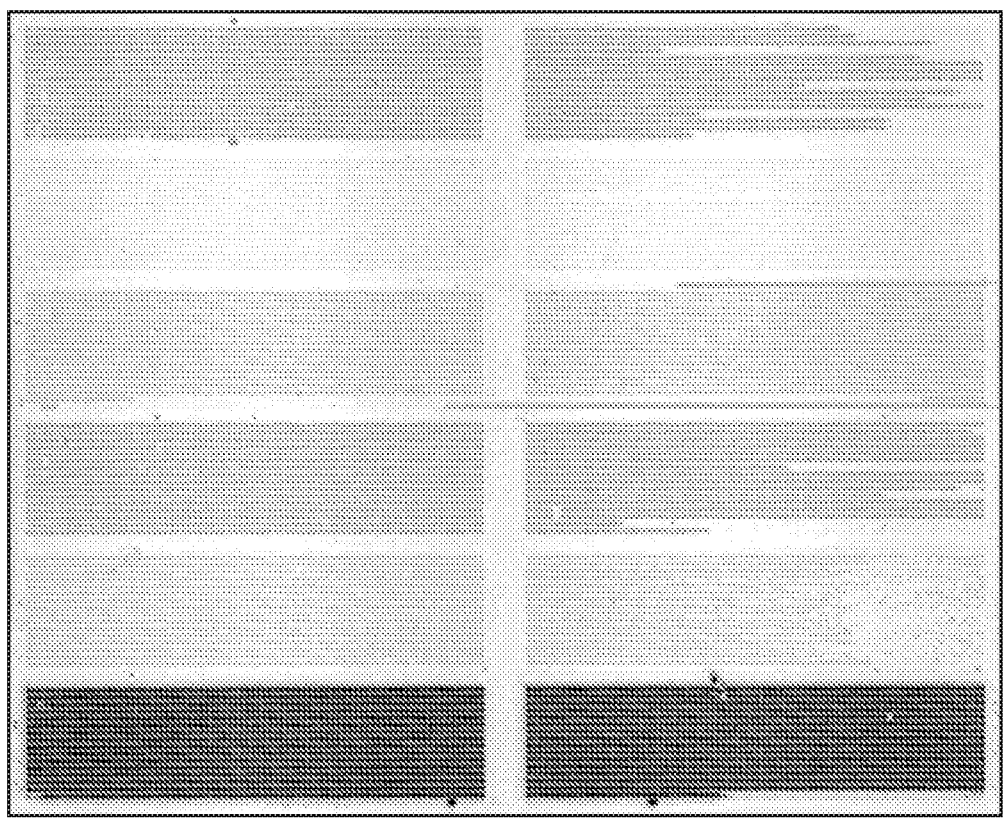
FIG. 15 shows a fluorescence image of a sample-loaded device according to certain aspects of the disclosure.

Sample loading occurred by adding sample (~60-80 μL for this design) to the inlet reservoir through the inlet with a pipette. In some embodiments the pipette was a multi-channel pipette. Once sample was loaded the device was loaded and secured onto the rotor and the rotor centrifuged at 400-800 RPM for 4-10 minutes, or until all the sample had settled in the fluidic compartments or outlet reservoir. FIG. 15 is a fluorescent image of a device loaded using this method. In this embodiment six arrays were loaded with sample. The arrays contained different sample solutions with different fluorescent intensities.

In particular arrays 2, 3 and 6 (counting from top to bottom) show greater than 94% digitization of sample into fluidic compartments.

Example 3

Thermalcycling of Microfluidic Devices

This example describes one embodiment of thermalcycling to perform dPCR of the microfluidic device.

Figure 16:
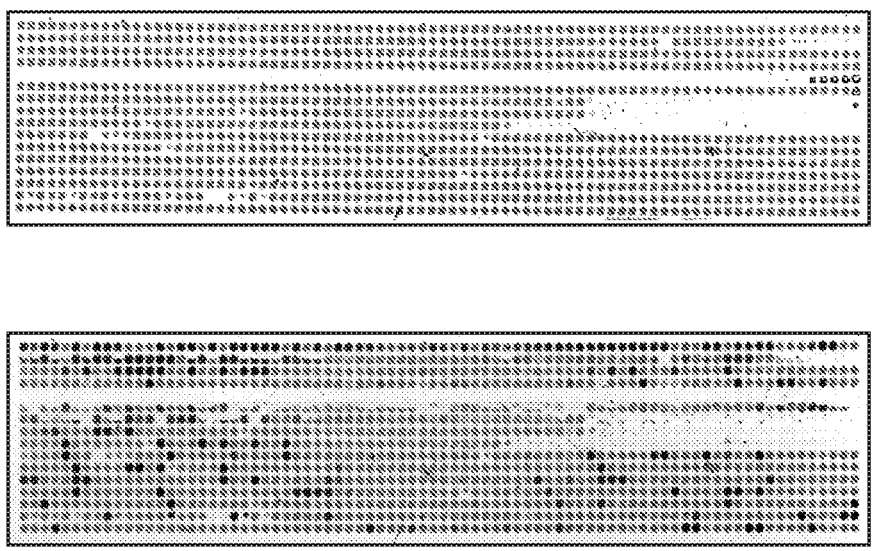
FIG. 16 shows images of a region of the device before (top) and after (bottom) thermalcycling.

The device was loaded as described in example 2. After loading the device was imaged. In this embodiment the device was imaged as described in example 1. In this embodiment the device was then placed on an in situ adapter of an Eppendorf Mastercycler thermalcycling instrument. Thermal paste had been put onto the adapter to improve the thermal contact and improve the accuracy of the actual temperature of the device and the programmed temperature. A thin layer of mineral oil was used to improve the thermal contact between the adapter and device by eliminating any air pockets that could be trapped between the devices. Thermalcylcing occurred based on the following program: 2 minutes at 95° C., then 35 cycles of 45 seconds at 95° C. and 60 seconds at 59° C. After thermalcycling the outside of the device was cleaned with isopropanol and the device was imaged again. FIG. 16 shows images of a region of the device before (Top) and after (Bottom) Thermalcycling. Positive and negative wells can be clearly identified after performing dPCR, and the overall integrity of the array was well maintained.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A microfluidic array for discretizing a fluidic sample, the array comprising:
   a proximal array portion comprising a fluid inlet port and a fluid outlet port;
   a distal array portion away from the proximal portion;
   one or more flow channels each comprising a length extending from the proximal array portion to the distal array portion, a proximal end in fluidic communication with the fluid inlet port, and a distal end in fluidic communication with the fluid outlet port, wherein at least one flow channel of the one or more flow channels comprises a change in cross-sectional dimension along the at least one flow channel's length from the proximal end to the distal end; and
   a plurality of fluidic compartments in fluidic communication with the one or more flow channels,
   wherein the change in cross-sectional dimension comprises a continuous tapering profile.

2. The array of claim 1, wherein the continuous tapering profile comprises a linear tapering profile, an exponential tapering profile, a polynomial tapering profile, or a combination thereof.

3. The array of claim 1, wherein the cross-sectional dimension comprises one or more of an average cross-sectional width, a maximum cross-sectional width, a minimum cross-sectional width, or a cross-sectional area.

4. A microfluidic device for discretizing a fluidic sample, the device comprising:
   a body comprising a proximal body portion and a distal body portion, and
   a plurality of microfluidic arrays as recited in claim 1 formed in the body such that the one or more flow channels of the plurality of microfluidic arrays extend substantially parallel to each other from the proximal body portion to the distal body portion.

5. A system for discretizing and analyzing fluidic samples, the system comprising:
   a rotor assembly comprising a central axis and a plurality of receptacles arranged radially around the central axis, at least one receptacle of the plurality of receptacles comprising a microfluidic device as recited in claim 4 such that the proximal body portion of the microfluidic device is positioned near the central axis and the distal body portion of the microfluidic device is positioned away from the central axis;
   a rotary actuator coupled to the rotor assembly; and
   one or more processors configured with instructions to cause the system to rotate the rotor assembly around the central axis using the rotary actuator.

6. The system of claim 5, further comprising a heating device configured to generate heat, wherein the one or more processors are configured with instructions to cause the system to apply heat to the microfluidic devices received in a receptacle of the plurality of receptacles using the heating device.

7. The system of claim 6, further comprising a cooling device, wherein the one or more processors are configured with instructions to cause the system to reduce a temperature of the microfluidic devices received in the plurality of receptacles using the cooling device.

8. The system of claim 6, further comprising a temperature sensor configured to obtain temperature data, wherein the one or more processors are configured with instructions to cause the system to adjust an amount of heat applied by the heating device in response to the temperature data.

9. The system of claim 5, further comprising an imaging device configured to obtain image data, wherein the one or more processors are configured with instructions to cause the system to obtain image data of the microfluidic devices received in a receptacle of the plurality of receptacles using the imaging device.

10. The system of claim 9, further comprising an illumination source.

11. The system of claim 9, wherein the plurality of microfluidic devices comprise a fluidic sample including a fluorophore, the illumination source is configured to produce light energy at an excitation wavelength of the fluorophore, and the imaging device is configured to measure light energy at an emission wavelength of the fluorophore.

12. The system of claim 5, wherein a first fluid is disposed within the microfluidic device, wherein the one or more processors are configured with instructions to cause discretization of a fluidic sample in the at least one microfluidic device and wherein the fluidic sample is immiscible with the first fluid.

13. A method for discretizing and analyzing a fluidic sample, the method comprising:
   providing a microfluidic device recited in claim 4;
   applying a fluidic sample to the fluid inlet ports of the microfluidic device, the fluidic sample comprising a plurality of discrete analytes; and
   rotating the microfluidic device such that the plurality of discrete analytes are driven into a subset of the plurality of fluidic compartments of the microfluidic device.

14. The method of claim 13, further comprising applying heat to the microfluidic device in order to amplify the analytes present in the microfluidic device, wherein said analytes are nucleic acids.

15. The method of claim 14, further comprising obtaining image data using an imaging device by applying light energy to the plurality of fluidic compartments; and
measuring a fluorescence signal to determine presence or absence of said analytes within the plurality of fluidic compartments.

16. The method of claim 15, wherein obtaining the image comprises translating or rotating the imaging device in order to align the microfluidic device with the imaging device.

17. A microfluidic array for discretizing a fluidic sample, the array comprising:
a proximal array portion comprising a fluid inlet port and a fluid outlet port;
a distal array portion away from the proximal portion;
one or more flow channels each comprising a length extending from the proximal array portion to the distal array portion, a proximal end in fluidic communication with the fluid inlet port, and a distal end in fluidic communication with the fluid outlet port, wherein at least one flow channel of the one or more flow channels comprises a change in cross-sectional dimension along the at least one flow channel's length from the proximal end to the distal end; and
a plurality of fluidic compartments in fluidic communication with the one or more flow channels,
wherein at least one flow channel of the one or more flow channels comprises an increasing cross-sectional dimension along the length from the proximal end to the distal end.

* * * * *

UNITED STATES PATENT AND TRADEMARK OFFICE
CERTIFICATE OF CORRECTION

PATENT NO.         : 10,794,925 B2                                         Page 1 of 1
APPLICATION NO.    : 15/741462
DATED              : October 6, 2020
INVENTOR(S)        : D. Chiu et al.

It is certified that error appears in the above-identified patent and that said Letters Patent is hereby corrected as shown below:

In the Claims

| Column | Line | |
|---|---|---|
| 37 | 8 | In Claim 15, "determine presence" to -- determine the presence -- |

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*